US007053207B2

(12) United States Patent
Wengel

(10) Patent No.: US 7,053,207 B2
(45) Date of Patent: *May 30, 2006

(54) L-RIBO-LNA ANALOGUES

(75) Inventor: Jesper Wengel, Odense (DK)

(73) Assignee: Exiqon A/S, Vedbaek (DK)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

This patent is subject to a terminal disclaimer.

(21) Appl. No.: 09/565,699

(22) Filed: May 4, 2000

(65) Prior Publication Data
US 2003/0087230 A1 May 8, 2003

Related U.S. Application Data

(60) Provisional application No. 60/176,206, filed on Jan. 14, 2000, provisional application No. 60/158,709, filed on Oct. 8, 1999, provisional application No. 60/133,273, filed on May 10, 1999.

(30) Foreign Application Priority Data

May 4, 1999 (DK) ............... 1999 00603
Sep. 1, 1999 (DK) ............... 1999 01225
Jan. 11, 2000 (DK) ............... 2000 00032

(51) Int. Cl.
C07H 21/02 (2006.01)
C07H 21/04 (2006.01)
C12Q 1/68 (2006.01)

(52) U.S. Cl. .................. 536/25.3; 536/22.1; 536/23.1; 536/24.3; 435/6; 435/325

(58) Field of Classification Search ............ 435/6, 435/91.31; 536/27.11, 23.1; 544/264, 243; 514/45
See application file for complete search history.

(56) References Cited

U.S. PATENT DOCUMENTS

| 4,837,312 | A | 6/1989 | Dervan et al. ............... 536/27 |
| 5,559,101 | A * | 9/1996 | Weis et al. ................... 514/45 |
| 6,436,640 | B1 * | 8/2002 | Simmons et al. .............. 435/6 |
| 6,525,191 | B1 | 2/2003 | Ramasamy ............... 536/28.7 |
| 6,670,461 | B1 | 12/2003 | Wengel et al. |
| 6,794,499 | B1 | 9/2004 | Wengel et al. |
| 2002/0068708 | A1 * | 6/2002 | Wengel et al. ............... 514/44 |
| 2003/0018186 | A1 | 1/2003 | Ramasamy et al. ........ 536/28.7 |

FOREIGN PATENT DOCUMENTS

| EP | 0538194 B1 | 4/1999 |
| WO | WO 93/07883 | 4/1993 |
| WO | WO98/22489 | 5/1998 |
| WO | WO 98/39352 | * 9/1998 |
| WO | WO98/39352 | 9/1998 |
| WO | WO99/14226 | 3/1999 |

OTHER PUBLICATIONS

Obika et al. Synthesis and conformation of 3'-O, 4'-C-methyleneribonucleosides, novel bicyclic nucleoside analogues for 2',5'-linked oligonucleotide modification. Chemical Communications, 1997, pp. 1643-1644.*
Koshkin et al. LNA(Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition. Tetrahedron 54, pp. 3607-3630, 1998.*
Crooke, S.T. Antisense Research and Application, Chapter 1, Basic Principles of Antisense Therapeutics, (1998), pp. 1-50. Springer-Verlag Press, Berlin, Heidelber, New York.*
Tarkoy et al., Helv. Chim. Acta, 76:481 (1993).
Tarkoy et al., Angew. Chem., Int. Ed. Engl., 32:1432 (1993).
Egli et al., J. Am. Chem. Soc., 115:5855 (1993).
Tarkoy et al., Helv. Chim. Acta, 77:716 (1994).
Bolli et al., Angew. Chem., Int. Ed. Engl., 34:694 (1995).
Bolli et al., Helv. Chim. Acta, 78:2077 (1995).
Litten et al., Bioorg. Med. Chem. Lett., 5:1231 (1995).
Litten et al., Helv. Chim. Acta, 79:1129 (1996).
Bolli et al., Chem. Biol., 3:197 (1996).
Bolli et al., Nucleic Acids. Res., 24:4660 (1996).
K.H. Altmann et al., Tetrahedron Lett., 35::2331 (1994).
K. H. Altmann et al., Tetrahedron Lett., 35:7625 (1994).
Marquez et al., J. Med. Chem., 39:3739 (1996).
Ezzitouni et al., J. Chem. Soc., Perkin Trans., 1:1073 (1997).
Jones et al., J. Am. Chem. Soc., 115:9816 (1993).
Wang et al., Bioorg. Med. Chem. Lett., 7: 229 (1997).
Yannopoulus et al., Synlett, 378 (1997).
Chima, 36th IUPAC Congress, organized by the Swiss Chemical Society. Poster No. SB-B4: Steffens, R. and Leumann Ch. Tricyclo-DNA: synthesis, enzymatic stability, and pairing properties.
Nielsen, Master Thesis (Odense University, Denmark), p. 67-71 (1995).
Youssefyeh et al., J. Org. Chem., 44:1301 (1979).
Jones et al., J. Org. Chem., 44:1309 (1979).
Yang et al., Tetrahedron Lett., 33:37 (1992).
Thrane et al., Tetrahedron, 51:10389 (1995).
Nielsen et al., Bioorg. Med. Chem., 3:1493 (1995).

(Continued)

Primary Examiner—Janet L. Epps-Ford
(74) Attorney, Agent, or Firm—Peter F. Corless; Stephana E. Patton; Edwards, Angell, Palmer & Dodge, LLP

(57) ABSTRACT

Provided are L-ribo bicyclic nucleotide compounds as well as syntheses of such compounds. The nucleoside compounds of the invention are useful in forming oligonucleotides that can produce nucleobase specific duplexes with complementary single stranded and double stranded nucleic acids.

29 Claims, 4 Drawing Sheets

OTHER PUBLICATIONS

Freier et al., *Nucleic Acid Research*, 25:4429-4443 (1997).
Haly et al., *SYNLETT*, 687-689 (1996).
Zou et al., *Tetrahedron Lett.*, 37:941-944 (1996).
Herdewijn., *Liebigs Ann.*, 1337-1348 (1996).
Obika et al., *Tetrahedron Lett.*, 39:5401-5404 (1998).
Obika et al., *Tetrahedron Lett.*, 38:8735-8738 (1997).
7th Antisense Symposium, Nov. 21-22, 1997. Poster No. 32 and 33: Obika, D.N.; Morio, K. and Imanishi, T. Synthesis and properties of oligonucleotides containing novel bicyclic nucleosides with a fixed N-form sugar puckering.
Chima, 36th IUPAC Congress, organized by the Swiss Chemical Society. Poster No. SB-B12: Egtger, A. and Leumann Ch. Designe, synthesis and properties of bicyclo [3.2.1]-amio nucleic acids.
Chima, 36th IUPAC Congress, organized by the Swiss Chemical Society. Poster No. SB-B5: Epple, C. Ch., Pompizi, I. and Leumann Ch. Bicyclo [3.2.1]-DNA: an oligonucleotide analogue with a conformationally preorganized Phosphodiester backbone and a flexible sugar-base linkage.
Sep. 6-10, 1998: 13th International Round Table—Nucleoside, Nucleotides and their Biological Applications, Montpeilleir: Oral Communication 1: Wang, G. and Gunic, E. "Conformationally Locked Nucleoside Analogs. Synthesis of 2'-Deoxy-2'-C, 4'-C-Bridged Bicyclic Nucleoside".
Sep. 6-10, 1998: 13th International Round Table—Nucleoside, Nucleotides and their Biological Applications, Montpeilleir: Poster No. 288: Meldgaard, M. et al., "LNA (Locked Nucleic Acids): Synthesis and Thermal Denaturation Studies".
Sep. 6-10, 1998: 13th International Round Table—Nucleoside, Nucleotides and their Biological Applications, Montpeilleir: Poster No. 287 and Proceeding: Koshkin, A. A. et al., "Locked Nucleic Acids as synthetic RNA Mimics for Effective Complementary Recognition."
Sep. 6-10, 1998: 13th International Round Table—Nucleoside, Nucleotides and their Biological Applications, Montpeilleir: Poster No. 67: Nielsen, P. and Wengel, J. "A New Convergent Synthetic Approach Towards a-and β-LNA (Locked Nucleic Acids)".
Oct. 8, 1998: Antisense 98, Targeting the Molecularl Basis of Disease: Poster No. 24: Havsteen, M. et al., "LNA (Locked Nucleic Acids): A new Class of High Affinity Nucleic Acids With Prime Potential as Antisense and Antigene Agents".
Jan. 21, 1998: National Seminar on Perspectives in Interfacial Areas of Chemistry and Biology, Delhi University: Wengel, J. "LNA (Locked Nucleic Acids): Synthesis and High Affinity Nucleic Acid Recognition—Stop the Twisting."
27 Marts 1998: Workshop of Young European Bioorganic Chemists, Munchen: Wengel, J. "LNA (Locked Nucleic Acids): Synthesis and High Affinity Nucleic Acid Recognition—Stop the Twisting."
Aug. 20, 1998: Årsmødet for Center for Medicinsk Biotecknologi, KVL: Wengel, J. "LNA (Locked Nucleic Acids)"ations, Montpeilleir: Oral Communication 1: Wang, G. and Gunic, E. "Conformationally Locked Nucleoside Analogs. Synthesis of 2'-Deoxy-2'C, 4'-C-Bridged Bicyclic Nucleoside".
Sep. 7, 1998: 13th International Round Table—Nucleoside, Nucleotides and their Biological Applications, Montpeilleir:
Oral Communication 2: Wengel, J. "LNA (locked Nucleic Acids)".
Sep. 8, 1998: Meeting in Lund, Sweden: Jakobsen, M. H. "LNA (Locked Nucleic Acids): A new Class of High Affinity Nucleic Acids With Prime Potential as Antisense and Antigene Agents".
Nielsen et al., *J. Chem. Soc., Perkin Trans.*, 1:3423-3433 (1997).
Nielsen et al., *Chem. Commun.*, 9:825-826 (1997).
Singh et al., *Chem. Commun.*, 455-456 (1998).
Koshkin et al., *Tetrahedron*, 54:36073630 (1998).
Koshkin et al., *Tetrahedron Lett.*, 39:4381-8384 (1998).
Singh et al., *Chem. Commun.*, 1237-1248 (1998).
Singh et al., *J. Org. Chem.*, 63:6078-6079 (1998).
Christensen et al., *J. Am. Chem. Soc.*, 120:5458-5463 (1998).
Koshkin et al., *J. Org. Chem.*, 63:2778-2781 (1998).
Kumar et al., *Bioorg. Med. Chem. Lett.*, 8:2219-2222 (1998).
Wengel et al., *Acc. Chem. Res.*, 32:301-310 (1999).
Koshkin et al., *J. Am. Chem. Soc.*, 120:13252-13253 (1998).
Singh et al., *J. Org. Chem.*, 10035-10039 (1998).
Nielsen et al., *Chem. Commun.*, 2645-2646 (1998).
Wengel et al., *Nucleosides Nucleoties*, 18:1365-1370 (1999).
Nielsen et al., *Nucleosides Nucleotides*, 18:701-702 (1999).
Kærno et al., *Chem. Commun.*, 657-658 (1999).
Rajwanshi et al., *J. Chem. Soc., Perkin Trans.*, 1:1407-1414 (1999).
Raunkjær et al., *J. Chem. Soc., Perkin Trans.*, 1:2543-2551 (1999).
Rajwanshi et al., *Chem. Commun.*, 1395-1396 (1999).
Pfundheller et al., *Nucleosides Nucleotides*, 18:2017-2030 (1999).
Rajwanshi et al., *Chem. Commun.*, 2073-2074 (1999).
Nielsen et al., *J. Biomol. Struc. Dyn.*, 17:175-191 (1999).
Nielsen et al., *Bioconjugate Chem.*, 11:228-238 (2000).
Rajwanshi et al., *Angewandte Chemie*, 39:1656-1659 (2000).
Minasov et al., *Biochemistry*, 39:3525 (2000).
Wahlesttedt et al., *Proc. Natl. Acad. Sci. USA*, 97:5633-5638 (2000).
Obika et al., *Tetrahedron Lett.*, 40:6465-6468 (1999).
Obika et al., *Tetrahedron Lett.*, 41:215-219 (1999).
Obika et al., *J. Chem. Soc., Chem. Commun.*, 2423-2424 (1999).
Wang et al., *Bioorg. Med. Chem. Lett.*, 9:1147-1150 (1999).
Obika et al., *Tetrahedron Lett.*, 41:221-224 (1999).
Obika et al., *Bioorg. Med. Chem. Lett.*, 9:515-518 (1999).
Obika et al., *Tetrahedron Lett.*, 39:5401-5405 (1998).
Imanishi et al., *J. Synth. Org. Chem.*, 57:959-980 (1999).
Chemical Abstracts, vol. 70, No. 1, Abstract No. 3737B (1969).
*Monatsch. Chem.*, 99(5):2111-2120 (1968).
Sorensen, et al., "α-L-ribo-Configured Locked Nucleic Acid (α-L-LNA): Synthesis and Properties", JACS Articles, published on Web Feb. 14, 2002, vol. 124, No. 10, 2002, J.Am. Chem. Doc.
Hakansson, et al., The Adenine Derivative of α-L-LNA (α-L-ribo Configured Locked Nucleic Acid): Synthesis and High-Affinity Hybridization towards DNA, RNA, LNA and α-L- LNA Complementary Sequences, Bioorganic & Medicinal Letters 11 (2001) 935-938.
Bergstrom, et al., "Synthesis, Structure, and Deoxyribonucleic Acid Sequencing with a Universal Nucleoside: 1-(2'-Deoxy-β-D-ribofuranosyl)-3-nitropyrrole", J.Am. Chem.Soc. 1995, 117, 1201-1209.

Sund, et al., "Synthesis of C-Branched Spermine Tethered Oligoo-DNA and the Thermal Stability of the Duplexes and Triplexes", Tetrahedron vol. 52, No. 37, pp. 12275-12290, 1996.

T. Imanishi, et al. "Synthesis And Property Of Novel Conformationally Constrained Nucleoside And Oligonucleotide Analogs", The Sixteenth International Congress of Heterocyclic Chemistry, Aug. 10-15, 1997, four pages.

U.S. Appl. No. 10/208,650, filed Jul. 29, 2002, Wengel et al.

* cited by examiner

L-RIBO-LNA ANALOGUES

The present application claims the benefit of U.S. provisional application No. 60/133,273, filed May 10, 1999; U.S. provisional application No. 60/158,709, filed Oct. 8, 1999; and U.S. provisional application No. 60/176,206, filed Jan. 14, 2000, all incorporated herein by reference in their entirety.

FIELD OF THE INVENTION

The present invention relates to the field of L-ribo-configurated bicyclic nucleoside analogues and to the synthesis of such nucleoside analogues which are useful in the formation of synthetic oligonucleotides capable of forming nucleobase specific duplexes with complementary single stranded and double stranded nucleic acids. The invention also relates to the field of L-ribo-configurated bicyclic nucleoside analogues which may be used as therapeutic drugs and which may be incorporated in oligonucleotides.

BACKGROUND OF THE INVENTION

Synthetic oligonucleotides are widely used compounds in disparate fields such as molecular biology and DNA-based diagnostics and therapeutics.

General Considerations

To be useful in the extensive range of the different applications outlined above, oligonucleotides have to satisfy a large number of different requirements. As therapeutics, for instance, a useful oligonucleotide must be able to penetrate the cell membrane, have good resistance to extra- and intracellular nucleases and preferably have the ability to recruit endogenous enzymes like RNAseH. In DNA-based diagnostics and molecular biology, other properties are important such as, for instance, the ability of oligonucleotides to act as efficient substrates for a wide range of different enzymes evolved to act on natural nucleic acids, such as e.g. polymerases, kinases, ligases and phosphatases. The fundamental property of oligonucleotides, however, which underlies all uses is their ability to recognise and hybridise sequence specifically to complementary single stranded nucleic acids employing either Watson-Crick hydrogen bonding (A-T and G-C) or other hydrogen bonding schemes such as the Hoogsteen mode. There are two important terms, affinity and specificity, commonly used to characterise the hybridisation properties of a given oligonucleotide. Affinity is a measure of the binding strength of the oligonucleotide to its complementary target sequence (expressed as the thermostability ($T_m$) of the duplex). Each nucleobase pair in the duplex adds to the thermostability and thus affinity increases with increasing size (number of nucleobases) of the oligonucleotide. Specificity is a measure of the ability of the oligonucleotide to discriminate between a fully complementary and a mismatched target sequence. In other words, specificity is a measure of the loss of affinity associated with mismatched nucleobase pairs in the target.

At constant oligonucleotide size, the specificity increases with increasing number of mismatches between the oligonucleotide and its targets (i.e. the percentage of mismatches increases). Conversely, specificity decreases when the size of the oligonucleotide is increased at a constant number of mismatches (i e. the percentage of mismatches decreases). Stated another way, an increase in the affinity of an oligonucleotide occurs at the expense of specificity and vice-versa.

Given the shortcomings of natural oligonucleotides, new approaches for enhancing specificity and affinity are highly desirable for DNA-based therapeutics, diagnostics and for molecular biology techniques in general.

Conformationally Restricted Nucleosides

It is known that oligonucleotides undergo a conformational transition in the course of hybridising to a target sequence, from the relatively random coil structure of the single stranded state to the ordered structure of the duplex state.

Thus, conformational restriction has in recent years been applied to oligonucleotides in the search for analogues displaying improved hybridisation properties compared to the unmodified (2'-deoxy)oligonucleotides. For example bicyclo[3.3.0]nucleosides with an additional C-3',C-5'-ethano-bridge (M. Tarköy, M. Bolli, B. Schweizer and C. Leumann, *Helv. Chem. Acta,* 1993, 76, 481; Tarköy and C. Leumann, *Angew. Chem., Int. Ed. Engl.,* 1993, 32, 1432; M. Egli, P. Lubini, M. Dobler and C. Leumann, *J. Am. Chem. Soc.,* 1993, 115, 5855; M. Tarköy, M. Bolli and C. Leumann, *Helv. Chem. Acta,* 1994, 77, 716; M. Bolli and C. Leumann, *Angew. Chem., Int. Ed. Engl.,* 1995, 34, 694; M. Bolli, P. Lubini and C. Leumann, *Helv. Chem. Acta,* 1995, 78, 2077; J. C. Litten, C. Epple and C. Leumann, *Bioorg. Med. Chem. Lett.,* 1995, 5, 1231; J. C. Litten and C. Leumann, *Helv. Chem. Acta,* 1996, 79, 1129; M. Bolli, J. C. Litten, R. Schültz and C. Leumann, *Chem. Biol.,* 1996, 3, 197, M. Bolli, H. U. Trafelet and C. Leumann, *Nucleic Acids Res.,* 1996, 24, 4660), bicarbocyclo[3.1.0]nucleosides with an additional C-1',C6'- or C6',C4'-methano-bridge (K.-H. Altmann, R. Kesselring, E. Francotte and G. Rihs, *Tetrahedron Lett.,* 1994, 35, 2331; K.-H. Altmann, R. Imwinkelned, R. Kesselring and G. Rihs, *Tetrahedron Lett.,* 1994, 35, 7625; V. E. Marquez, M. A. Siddiqui, A. Ezzitouni, P. Russ, J. Wang, R. W. Wagner and M. D. Matteucci, *J. Med. Chem.,* 1996, 39, 3739; A. Ezzitouni and V. E. Marquez, *J. Chem. Soc., Perkin Trans.* 1, 1997, 1073), bicyclo[3.3.0]- and [4.3.0] nucleoside containing an additional C-2',C-3'-dioxalane ring synthesised as a dimer with an unmodified nucleoside where the additional ring is part of the internucleoside linkage replacing a natural phosphordiester linkage (R. J. Jones, S. Swaminathan, J. F. Milagan, S. Wadwani, B. S. Froehler and M. Matteucci, *J. Am. Chem. Soc.,* 1993, 115, 9816; J. Wang and M. D. Matteucci, *Bioorg. Med. Chem. Lett.,* 1997, 7, 229), dimers containing a bicyclo[3.1.0]nucleoside with a C-2',C-3'-methano bridge as part of amide- and sulfonamide-type internucleoside linkages (C. G. Yannopoulus, W. Q. Zhou, P. Nower, D. Peoch, Y. S. Sanghvi and G. Just, *Synlett,* 1997, 378), bicyclo[3.3.0] glucose-derived nucleoside analogue incorporated in the middle of a trimer through formacetal internucleoside linkages (C. G. Yannopoulus. W. Q. Zhou, P. Nower, D. Peoch, Y. S. Sanghvi and G. Just, *Synlett,* 1997, 378) and bicyclic [4.3.0]- and [3.3.0]nucleosides with additional C-2',C-3'-connected six- and five-membered ring (P. Nielsen, H. M. Pfundheller, J. Wengel, *Chem. Commun.,* 1997, 826; P. Nielsen, H. M. Pfundheller, J. Wengel, XII International Roundtable: Nucleosides, Nucleotides and Their Biological Applications; La Jolla, Calif., Sep. 15–19, 1996; Poster PPI 43) have been synthesised and incorporated into oligodeoxynucleotides. Unfortunately, oligonucleotides comprising these analogues form in most cases less stable duplexes with complementary nucleic acids compared to the unmodified oligonucleotides. In cases where a moderate improvement in duplex stability is observed, this relates only to either a DNA or an RNA target, or it relates to fully but not partly modified oligonucleotides or vice versa.

An appraisal of most of the reported analogues are further complicated by the lack of data on analogues with G, A and C nucleobases and lack of data indicating the specificity and mode of hybridisation. In many cases, synthesis of the reported monomer analogues is very complex while in other cases the synthesis of fully modified oligonucleotides is incompatible with the widely used phosphoramidite chemistry standard.

Recently, oligomers comprising Locked Nucleic Acids (LNA) have been reported (Nielsen, P., Pfundheller, H. M., Olsen, C. E. and Wengel, J., *J. Chem. Soc., Perkin Trans.* 1, 1997, 3423; Nielsen, P., Pfundheller, H. M., Wengel, J., *Chem. Commun.*, 1997, 9, 825, Christensen, N. K., Petersen, M., Nielsen, P., Jacobsen, J. P. and Wengel, J., *J. Am. Chem. Soc.*, 1998, 120, 5458; Koshkin, A. A. and Wengel, J., *J. Org. Chem.*, 1998, 63, 2778; Obika, S., Morio, K.-I., Hari, Y. and Imanishi, T., *Bioorg. Med. Chem. Lett.*, 1999, 515). Interestingly, incorporation of LNA monomers containing a 2'-O,4'-C-methylene bridge into an oligonucleotide sequence led to unprecedented improvement in the hybridisation ability of the modified oligonucleotide (Singh, S. K., Nielsen, P., Koshkin, A. A., Olsen, C. E. and Wengel, J., *Chem. Commun.*, 1998, 455; Koshkin, A. K., Singh, S. K., Nielsen, P., Rajwanshi, V. K., Kumar, R., Meldgaard, M., Olsen, C. E., and Wengel, J., *Tetrahedron*, 1998, 54, 3607; Koshkin, A. A. Rajwanshi, V. K., and Wengel, J., *Tetrahedron Lett.*, 1998, 39, 4381; Singh, Sanjay K. and Wengel, J., *Chem. Commun*, 1998, 1247; Kumar, R., Singh, S. K, Koshkin, A. A., Rajwanshi, V. K., Meldgaard, M., and Wengel. J., *Bioorg. Med. Chem. Lett.*, 1998, 8, 2219; Obika, S. et al. *Tetrahedron Lett.*, 1997, 38, 8735; Obika, S. et al. *Tetrahedron Left.*, 1998, 39, 5401, Singh, S. K., Kumar, R., and Wengel, J., *J. Org. Chem.*, 1998, 63, 6078; Koshkin, A. A., Nielsen, P., Meldgaard, M., Rajwanski, V. K., Singh, S. K., and Wengel, J., *J. Am. Chem. Soc.*, 1998, 120, 13252; Singh, S. K., Kumar, R., and Wengel, J., *J. Org. Chem.*, 1998, 63, 10035). Oligonucleotides comprising these LNA monomers and the corresponding 2'-thio-LNA analogue form duplexes with complementary DNA and RNA with thermal stabilities not previously observed for bi- or tricyclic nucleosides modified oligonucleotides ($\Delta T_m$/modification=+3 to +11° C.) and show improved selectivity.

In a series of papers, Seela et al. have studied xylo-DNA (FIG. 1, Base=adenin-9-yl, cytosin-1-yl, guanin-9-yl or thymin-1-yl) comprising one or more 2'-deoxy-β-D-xylofuranosyl nucleotide monomers (Rosemeyer, H.; Seela, F. *Helv. Chem. Acta* 1991, 74, 748; Rosemeyer, H.; Krecmerova, M.; Seela, F. *Helv. Chem. Acta* 1991, 74, 2054; Seela, F.; Wörner, Rosemeyer, H. *Helv. Chem. Acta* 1994, 77, 883; Seela, F.; Heckel, M.; Rosemeyer, H. *Helv. Chem. Acta* 1996, 79, 1451; Rosemeyer, H.; Seela, F. *Nucleosides Nucleotides*, 1995, 14, 1041; Schoeppe, A.; Hinz, H.-J., Rosemeyer, H.; Seela, F. *Eur. J. Biochem.* 1996, 239, 33). Compared with the corresponding natural 2'-deoxy-β-D-ribofuranosyl oligonucleotides, xylo-DNA, generally, display a mirror-image-like secondary structure, entropically favourable duplex formation, increased stability towards exonucleases, and, for oligonucleotides comprising a small number of 2'-deoxy-β-D-xylofuranosyl monomers, decreased thermal affinity towards complementary DNA (Rosemeyer, H.; Seela, F. *Helv. Chem. Acta* 1991, 74, 748; Rosemeyer, H.; Krecmerova, M.; Seela, F. *Helv. Chem. Acta* 1991, 74, 2054; Seela, F.; Wörner, Rosemeyer, H. *Helv. Chem. Acta* 1994, 77, 883; Seela, F.; Heckel, M.; Rosemeyer, H. *Helv. Chem. Acta* 1996, 79, 1451).

SUMMARY OF THE INVENTION

Based on the above and on the remarkable properties of the 2'-O,4'-C-methylene bridged LNA monomers it was decided to synthesis oligonucleotides comprising one or more 2'-O,4'-C-methylene-α-L-ribofuranosyl nucleotide monomer(s). Computer modeling on α-L-ribo-LNA monomers likewise indicates an S-type conformation of the furanose ring. Thus, the aim of this work was to synthesis 2'-O,4'-C-methylene-α-L-ribofuranosyl nucleotide monomer and to study the thermal stability of oligonucleotides comprising this monomer. The results show that modified L-ribo-LNA is useful for high-affinity targeting of complementary nucleic acids. When taking into consideration the inverted stereochemistry at C-3' and C-4' this is a surprising fact.

Thus, the present inventors have now provided novel LNA nucleoside analogues (L-ribo-LNAs) and oligonucleotides having L-ribo-LNA nucleoside analogues included therein. The novel L-ribo-LNA nucleoside analogues have been synthesised with thymine as the nucleobase but can easily be synthesised with the other four nucleobases thereby providing a full set of nucleoside analogues for incorporation in oligonucleotides.

The present invention relates to oligomers comprising at least one nucleoside analogue (hereinafter termed "L-ribo-LNA") of the general formula I

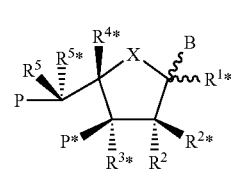

wherein X is selected from —O—, —S—, —N($R^{N*}$)—, —C($R^6R^{6*}$)—;

B is selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands;

P designates the radical position for an internucleoside linkage to a succeeding monomer, or a 5'-terminal group, such internucleoside linkage or 5'-terminal group optionally including the substituent $R^5$ or equally applicable the substituent $R^{5*}$;

P* designates an internucleoside linkage to a preceding monomer, or a 3'-terminal group;

$R^{2*}$ and $R^{4*}$ designate biradicals consisting of 1–4 groups/atoms selected from —C($R^aR^b$)—, —C($R^a$)=C($R^a$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di ($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where to geminal substituents $R^a$ and $R^b$ together may designate optionally substituted methylene olefin (=$CH_2$);

each of the substituents $R^{1*}$, $R^2$, $R^{3*}$, $R^5$, $R^{5*}$, $R^6$, and $R^{6*}$ which are present independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$)— where $R^N$ is selected from hydrogen and $C_{1-4}$-alkyl, and where two adjacent (non-geminal) substituents may designate an additional bond resulting in a double bond; and $R^{N*}$, when present, is selected from hydrogen and $C_{1-4}$-alkyl;

and basic salts and acid addition salts thereof.

The present invention furthermore relates to nucleoside analogues (L-ribo-LNAs) of the general formula II

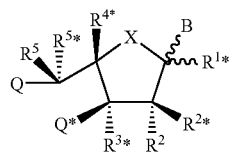

II wherein the substituent B is selected from nucleobases, DNA intercalators, photochemically active groups, thermochemically active groups, chelating groups, reporter groups, and ligands;

X is selected from —O—, —S—, —N($R^{N*}$)—, and —C($R^6R^{6*}$)—;

each of Q and Q' is independently selected from hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—$CH_2$—, Act-O—$CH_2$—, aminomethyl, Prot-N($R^H$)—$CH_2$—, Act-N($R^H$)—$CH_2$—, carboxymethyl, sulphonomethyl, where Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl; and $R^{2*}$ and $R^{4*}$ together designate a biradical selected from —O—, —(CR*R*)$_{r+s+1}$, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR*R*)$_{r+s}$—N(R*)—, —N(R*)—(CR*R*)$_{r+s}$—S—, and —S—(CR*R*)$_{r+s}$—N(R*)—;

wherein each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond, and each of r and s is 0–3 with the proviso that the sum r+s is 1–4, each of the present substituents $R^{1*}$, $R^2$, $R^{3*}$, $R^5$, $R^{5*}$, $R^6$, and $R^{6*}$ is indepepently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{1-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$)— where $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl;

and basic salts and acid addition salts thereof;

with the proviso that any chemical group (including any nucleobase), which is reactive under the conditions prevailing in oligonucleotide synthesis, is optionally functional group protected.

The present invention also relates to the use of the nucleoside analogues (L-ribo-LNAs) for the preparation of oligomers, and the use of the oligomers as well as the nucleoside analogues (L-ribo-LNAs) in diagnostics, molecular biology research, and in therapy.

DETAILED DESCRIPTION OF THE INVENTION

Figure 1:
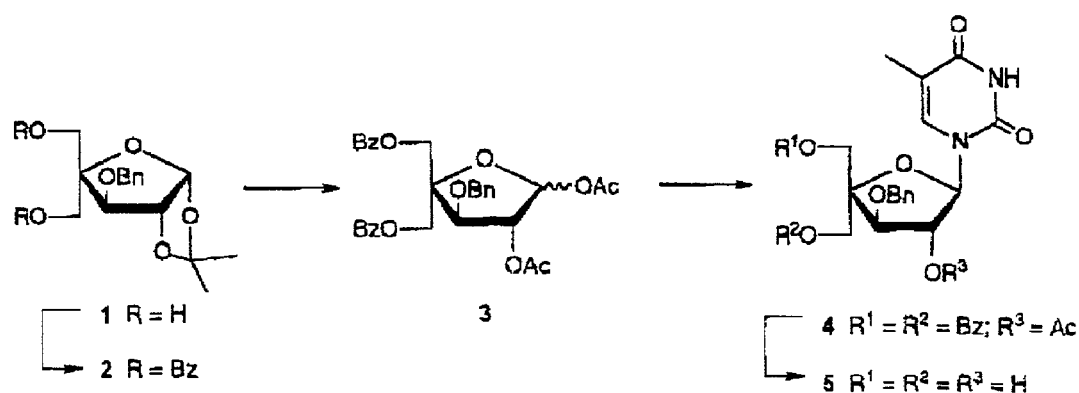
FIG. 1 illustrates syntheses of Examples 1–4.

When used herein, the term "L-ribo-LNA" (L-ribo-configured Locked Nucleoside Analogues) refers to L-ribo-configured bicyclic nucleoside analogues, either incorporated in the oligomer of the invention (general formula I) or as discrete chemical species (general formula II). The term "monomeric L-ribo-LNA" specifically refers to the latter case.

Oligomers and Nucleoside Analogues

As mentioned above, the present invention i.a. relates to novel oligomers (oligonucleotides) comprising one or more L-ribo-configured bicyclic nucleoside analogues (hereinafter termed "L-ribo-LNA").

Each of the possible L-ribo-LNAs incorporated in an oligomer (oligonucleotide) has the general formula I

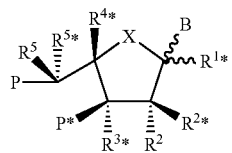

I wherein X is selected from —O— (the L-ribofuranose motif), —S—, —N($R^{N*}$)—, —C($R^6 R^{6*}$)—, where $R^6$, $R^{6*}$, and $R^{N*}$ are as defined further below. Thus, the L-ribo-LNAs incorporated in the oligomer comprises a 5-membered ring as an essential part of the bicyclic structure.

Among the possible 5-membered rings, the situations where X designates —O—, —S—, and —N($R^{N*}$) seem especially interesting, and the situation where X is —O— appears to be particularly interesting.

The substituent B may designate a group which, when the oligomer is complexing with DNA or RNA, is able to interact (e.g. by hydrogen bonding or covalent bonding or electronic interaction) with DNA or RNA, especially nucleobases of DNA or RNA. Alternatively, the substituent B may designate a group which acts as a label or a reporter, or the substituent B may designate a group (e.g. hydrogen) which is expected to have little or no interactions with DNA or RNA. Thus, the substituent B is preferably selected from hydrogen, hydroxy, optionally substituted $C_{1-4}$-alkoxy, optionally substituted $C_{1-4}$-alkyl, optionally substituted $C_{1-4}$-acyloxy, nucleobases, DNA intercalators, photochemically active groups, thermochemically active groups, chelating groups, reporter groups, and ligands.

In the present context, the terms "nucleobase" covers naturally occurring nucleobases as well as non-naturally occurring nucleobases. It should be clear to the person skilled in the art that various nucleobases which previously have been considered "non-naturally occurring" have subsequently been found in nature. Thus, "nucleobase" includes not only the known purine and pyrimidine heterocycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosine, $N^6,N^6$-ethano2,6-diaminopurine, 5-methylcytosine, 5-($C^3$–$C^6$)-alkynylcytosine, 5-fluorouracil, 5-bromouracil, pseudoiso-cytosine, 2-hydroxy-5-methyl-4-triazolopyridin, isocytosine, isoguanin, inosine and the "non-naturally occurring" nucleobases described in Benner et al., U.S. Pat. No. 5,432,272. The term "nucleobase" is intended to cover all of these examples as well as analogues and tautomers thereof. Especially interesting nucleobases are adenine, guanine, thymine, cytosine, and uracil, which are considered as the naturally occurring nucleobases in relation to therapeutic and diagnostic application in humans.

When used herein, the term "DNA intercalator" means a group which can intercalate into a DNA or RNA helix, duplex or triplex. Examples of functional parts of DNA intercalators are acridines, anthracene, quinones such as anthraquinone, indole, quinoline, isoquinoline, dihydroquinones, anthracyclines, tetracyclines, methylene blue, anthracyclinone, psoralens, coumarins, ethidium-halides, dynemicin, metal complexes such as 1,10-phenanthroline-copper, tris(4,7-diphenyl-1,10-phenanthroline)ruthenium-cobalt-enediynes such as calcheamicin, porphyrins, distamycin, netropcin, viologen, daunomycin. Especially interesting examples are acridines, quinones such as anthraquinone, methylene blue, psoralens, coumarins, and ethidium-halides.

In the present context, the term "photochemically active groups" covers compounds which are able to undergo chemical reactions upon irradiation with light. Illustrative examples of functional groups hereof are quinones, especially 6-methyl-1,4-naphtoquinone, anthraquinone, naphthoquinone, and 1,4-dimethyl-anthraquinone, diazirines, aromatic azides, benzophenones, psoralens, diazo compounds, and diazirino compounds.

In the present context "thermochemically reactive group" is defined as a functional group which is able to undergo thermochemically-induced covalent bond formation with other groups. Illustrative examples of functional parts thermochemically reactive groups are carboxylic acids, carboxylic acid esters such as activated esters, carboxylic acid halides such as acid fluorides, acid chlorides, acid bromide, and acid iodides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, and boronic acid derivatives.

In the present context, the term "chelating group" means a molecule that comprises more than one binding site and frequently binds to another molecule, atom or ion through more than one binding site at the same time. Examples of functional parts of chelating groups are iminodiacetic acid, nitrilotriacetic acid, ethylenediamine tetraacetic acid (EDTA), aminophosphonic acid, etc.

In the present context, the term "reporter group" means a group which is detectable either by itself or as a part of an detection series. Examples of functional parts of reporter groups are biotin, digoxigenin, fluorescent groups (groups which are able to absorb electromagnetic radiation, e.g. light or X-rays, of a certain wavelength, and which subsequently reemits the energy absorbed as radiation of longer wavelength; illustrative examples are dansyl (5-dimethylamino)-1-naphthalenesulfonyl), DOXYL (N-oxyl-4,4-dimethyloxazolidine), PROXYL (N-oxyl-2,2,5,5-tetramethylpyrrolidine), TEMPO (N-oxyl-2,2,6,6- tetramethylpiperidine), dinitrophenyl, acridines, coumarins, Cy3 and Cy5 (trademarks for Biological Detection Systems, Inc.), erytrosine, coumaric acid, umbelliferone, Texas Red, rhodamine, tetramethyl rhodamine, Rox, 7-nitrobenzo-2-oxa-1-diazole (NBD), pyrene, fluorescein, europium, ruthenium, samarium, and other rare earth metals), radioisotopic labels, chemiluminescence labels (labels that are detectable via the emission of light during a chemical reaction), spin labels (a free radical (e.g. substituted organic nitroxides) or other paramagnetic probes (e.g. $Cu^{2+}$, $Mg^{2+}$) bound to a biological molecule being detectable by the use of electron spin resonance spectroscopy), enzymes (such as peroxidases, alkaline phosphatases, β-galactosidases, and glucose oxidases), antigens, antibodies, haptens (groups which are able to combine with an antibody, but which cannot initiate an immune response by itself, such as peptides and steroid hormones), carrier systems for cell membrane penetration such as: fatty acid residues, steroid moieties (cholesterol), vitamin A, vitamin D, vitamin E, folic acid peptides for specific receptors, groups for mediating endocytose, epidermal growth factor (EGF), bradykinin, and platelet derived growth factor (PDGF). Especially interesting examples are biotin, fluorescein, Texas Red, rhodamine, dinitrophenyl, digoxigenin, ruthenium, europium, Cy5 and Cy3.

In the present context "ligand" means something which binds. Ligands can comprise functional groups such as: aromatic groups (such as benzene, pyridine, naphtalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulphides, primary amines, secondary amines, tertiary amines, hydrazines, epoxides, maleimides, $C_1$–$C_{20}$ alkyl groups optionally interrupted or terminated with one or more heteroatoms such as oxygen atoms, nitrogen atoms, and/or sulphur atoms, optionally comprising aromatic or mono/polyunsaturated hydrocarbons, polyoxyethylene such as polyethylene glycol, oligolpolyamides such as poly-β-alanine, polyglycine, polylysine, peptides, oligo/polysaccharides, oligolpolyphosphates, toxins, antibiotics, cell poisons, and steroids, and also "affinity ligands", i.e. functional groups or biomolecules that have a specific affinity for sites on particular proteins, antibodies. poly- and oligosaccharides, and other biomolecules.

It will be clear for the person skilled in the art that the above-mentioned specific examples under DNA intercalators, photochemically active groups, thermochemically active groups, chelating groups, reporter groups, and ligands correspond to the "active/functional" part of the groups in question. For the person skilled in the art, it is furthermore clear that DNA intercalators, photochemically active groups, thermochemically active groups, chelating groups, reporter groups, and ligands are typically represented in the form M—K— where M is the "active/functional" part of the group in question and where K is a spacer through which the "active/functional" part is attached to the 5-membered ring. Thus, it should be understood that the group B. in the case where B is selected from DNA intercalators, photochemically active groups, thermochemically active groups, chelating groups, reporter groups, and ligands, has the form M-K-, where M is the "active/functional" part of the DNA intercalator, photochemically active group, thermochemically active group, chelating group, reporter group, and ligand, respectively, and where K is an optional spacer comprising 1–50 atoms, preferably 1–30 atoms, in particular 1–15 atoms, between the 5-membered ring and the "active/functional" part.

In the present context, the term "spacer" means a thermochemically and photochemically non-active distance-making group and is used to join two or more different moieties of the types defined above. Spacers are selected on the basis of a variety of characteristics including their hydrophobicity, hydrophilicity, molecular flexibility and length (e.g. see Hermanson et. al., "Immobilized Affinity Ligand Techniques", Academic Press, San Diego, Calif. (1992), p. 137-ff). Generally, the length of the spacers are less than or about 400 Å, in some applications preferably less than 100 Å. The spacer, thus, comprises a chain of carbon atoms optionally interrupted or terminated with one or more heteroatoms, such as oxygen atoms, nitrogen atoms, and/or sulphur atoms. Thus, the spacer K may comprise one or more amide, ester, amino, ether, and/or thioether functionalities, and optionally aromatic or mono/polyunsaturated hydrocarbons, polyoxyethylene such as polyethylene glycol, oligo/polyamides such as poly-β-alanine, polyglycine, polylysine, and peptides in general, oligosaccharides, oligo/polyphosphates. Moreover the spacer may consist of combined units thereof. The length of the spacer may vary, taking into consideration the desired or necessary positioning and spatial orientation of the "active/functional" part of the group in question in relation to the 5-membered ring. In particularly interesting embodiments, the spacer includes a chemically cleavable group. Examples of such chemically cleavable groups include disulphide groups cleavable under reductive conditions, peptide fragments cleavable by peptidases and so forth.

In one embodiment of the present invention, K designates a single bond so that the "active/functional" part of the group in question is attached directly to the 5-membered ring.

In a preferred embodiment, the substituent B in the general formulae I and II is preferably selected from nucleobases, in particular from adenine, guanine, thymine, cytosine and uracil.

In the oligomers of the present invention (formula I), P designates the radical position for an internucleoside linkage to a succeeding monomer, or a 5'-terminal group. The first possibility applies when the L-ribo-LNA in question is not the 5'-terminal "monomer", whereas the latter possibility applies; when the L-ribo-LNA in question is the 5'-terminal "monomer". It should be understood (which also will be clear from the definition of internucleoside linkage and 5'-terminal group further below) that such an internucleoside linkage or 5'-terminal group may include the substituent $R^5$ (or equally applicable: the substituent $R^{5*}$) thereby forming a double bond to the group P. (5'-Terminal refers to the position corresponding to the 5'-carbon atom of a ribose moiety in a nucleoside)

On the other hand, P* designates the radical position for an internucleoside linkage to a preceding monomer or a 3'-terminal group. Analogously, the first possibility applies where the L-ribo-LNA in question is not the 3'-terminal "monomer", whereas the latter possibility applies when the L-ribo-LNA in question is the 3'-terminal "monomer" (3'-Terminal refers to the position corresponding to the 3'-carbon atom of a ribose moiety in a nucleoside).

In the present context, the term "monomer" relates to naturally occurring nucleosides, non-naturally occurring nucleosides, PNAs, LNAs and so forth as well as L-ribo-LNAs. Thus, the term "succeeding monomer" relates to the neighbouring monomer in the 5'-terminal direction and the "preceding monomer" relates to the neighbouring monomer in the 3'-terminal direction. Such succeeding and preceding monomers, seen from the position of an L-ribo-LNA monomer, may be naturally occurring nucleosides or non-naturally occurring nucleosides, or even further L-ribo-LNA monomers.

Consequently, in the present context (as can be derived from the definitions above), the term "oligomer" means an oligonucleotide modified by the incorporation of one or more L-ribo-LNA(s).

The crucial part of the present invention is the L-ribo-configuration of the 5-membered ring combined with the provision that $R^{2*}$ and $R^{4*}$ together designate a biradical forming a fused ring onto the 5-membered ring.

In the groups constituting the biradical(s), Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, carbamido, $C_{1-6}$-alkanoyloxy, sulphono. $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted. Moreover, two geminal substituents $R^a$ and $R^b$ together may designate optionally substituted methylene olefin (=$CH_2$ optionally substituted one or two times with substituents as defined as optional substituents for aryl).

In the present context, i.e. in the present description and claims, the orientation of the biradicals are so that the left-hand side represents the substituent with the lowest number and the right-hand side represents the substituent with the highest number, thus, when $R^{2*}$ and $R^{4*}$ together designate a biradical "—O—$CH_2$—", it is understood that the oxygen atom represents $R^{2*}$, thus the oxygen atom is e.g. attached to the position of $R^{2*}$, and the methylene group represents $R^{4*}$.

Considering the interesting possibilities for the structure of the biradical(s) in L-ribo-LNA(s) incorporated in oligomers according to the invention, it is believed that the biradical(s) constituted by pair(s) of non-geminal substituents preferably is/are selected from —(CR*R*)$_r$—Y—(CR*R*)$_s$—, —(CR*R*)$_r$—Y—(CR*R*)$_s$—Y—, —Y—(CR*R*)$_{r+s}$—Y—, —Y—(CR*R*)$_r$—Y—(CR*R*)$_s$—, —(CR*R*)$_{r+s}$—, —Y—, —Y—Y—, wherein each Y is independently selected from —O—, —S—, —Si(R*)$_2$—, —N(R*)—, >C=O, —C(=O)—N(R*)—, and —N(R*)—C(=O)—, each R* is independently selected from hydrogen, halogen, azido, cyano, nitro, hydroxy, mercapto, amino, mono- or di($C_{1-6}$-alkyl)amino, optionally substituted $C_{1-6}$-alkoxy, optionally substituted $C_{1-6}$-alkyl, DNA intercalators, photochemically active groups, thermochemically active groups, chelating groups, reporter groups, and ligands, and/or two adjacent (non-geminal) R* may together designate a double bond; and each of r and s is 0–4 with the proviso that the sum r+s is 1–4. Particularly interesting situations are those wherein each biradical is independently selected from —Y—, —(CR*R*)$_{r+s}$—, —(CR*R*)$_r$—Y—(CR*R*)$_s$—, and —Y—(CR*R*)$_{r+s}$—Y—wherein and each of r and s is 0–3 with the proviso that the sum r+s is 1–4.

Particularly interesting oligomers are those wherein the following criteria applies for the L-ribo-LNA(s) in the oligomers: $R^{2*}$ and $R^{4*}$ together designate a biradical selected from —O—, —S—, —N(R*)—, —(CR*R*)$_{r+s+1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR*R*)$_{r+s}$—N(R*)—, —N(R*)—(CR*R*)$_{r+s}$—S—, and —S—(CR*R*)$_{r+s}$—N(R*)—; wherein each of r and s is 0–3 with the proviso that the sum r+s is 1–4, and where R* is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

In one preferred embodiment, one group R* in the biradical of at least one LNA is selected from DNA intercalators, photochemically active groups, thermochemically active groups, chelating groups, reporter groups, and ligands (where the latter groups may include a spacer as defined for the substituent B).

In another preferred embodiment, one group R* in the biradical of at least one LNA is selected from hydrogen, hydroxy, optionally substituted $C_{1-6}$-alkoxy, optionally substituted $C_{1-6}$-alkyl, DNA intercalators, photochemically active groups, thermochemically active groups, chelating groups, reporter groups, and ligands, and any remaining substituents R* are hydrogen.

With respect to the substituents $R^{1*}$, $R^2$, $R^{3*}$, $R^5$, $R^{5*}$, $R^6$, and $R^{6*}$ present, independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy. $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-aminocarbonyl, amino-$C_{1-6}$-alkyl-aminocarbonyl, mono- and di($C_{1-6}$-alkyl)amino-$C_{1-6}$-alkyl-aminocarbonyl. $C_{1-6}$-alkylcarbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands (where the latter groups may include a spacer as defined for the substituent B), where aryl and heteroaryl may be optionally substituted, and where two geminal substituents together may designate oxo, thioxo, imino, or optionally substituted methylene, or together may form a spiro biradical consisting of a 1–5 carbon atom(s) alkylene chain which is optionally interrupted and/or terminated by one or more heteroatoms/groups selected from —O—, —S—, and —(NR$^N$)— where R$^N$ is selected from hydrogen and $C_{1-4}$-alkyl, and where two adjacent (non-geminal) substituents may designate an additional bond resulting in a double bond, and R$^{N*}$, when present, is selected from hydrogen and $C_{1-4}$-alkyl.

Preferably, each of the substituents $R^{1*}$, $R^2$, $R^{3*}$, $R^5$, $R^{5*}$, $R^6$, and $R^{6*}$ of the L-ribo-LNA(s), which are present, is independently selected from hydrogen, optionally substituted $C_{1-6}$-alkyl, optionally substituted $C_{2-6}$-alkenyl, hydroxy, $C_{1-6}$-alkoxy, $C_{2-6}$-alkenyloxy, carboxy, $C_{1-6}$-alkoxycarbonyl. $C_{1-6}$-alkylcarbonyl, formyl, amino, mono and di($C_{1-6}$-alkyl)amino, carbamoyl, mono- and di($C_{1-6}$-alkyl)-amino-carbonyl, $C_{1-6}$-alkyl-carbonylamino, carbamido, azido, $C_{1-6}$-alkanoyloxy, sulphono, sulphanyl, $C_{1-6}$-alkylthio, DNA intercalators, photochemically active groups, thermochemically active groups, chelating groups, reporter groups, and ligands, and halogen, where two geminal substituents together may designate oxo, and where $R^{N*}$, when present, is selected from hydrogen and $C_{1-4}$-alkyl.

In a preferred embodiment of the present invention, X is selected from —O—, —S—, and —$NR^{N*}$, in particular —O—, and each of the substituents $R^{1*}$, $R^2$, $R^{3*}$, $R^5$, $R^{5*}$, $R^6$, and $R^{6*}$ of the L-ribo-LNA(s), which are present, designate hydrogen.

In an even more preferred embodiment of the present invention, X is O, the substituents $R^{1*}$, $R^2$, $R^3$, $R^5$, and $R^{5*}$ designate hydrogen, and $R^{2*}$ and $R^{4*}$ of an L-ribo-LNA incorporated into an oligomer together designate a biradical, selected from —O—, —$(CH_2)_{0-1}$—O—$(CH_2)_{1-3}$—, —$(CH_2)_{0-1}$—S—$(CH_2)_{1-3}$—, —$(CH_2)_{0-3}$—$N(R^N)$—$(CH_2)_{1-3}$—, and —$(CH_2)_{2-4}$—, in particular from —O—$CH_2$—, —S—$CH_2$—, and —$NR^H$—$CH_2$—. Generally, with due regard to the results obtained so far, it is preferred that the biradical constituting $R^{2*}$ and $R^{4*}$ forms a two atom bridge, i.e. the biradical forms a five membered ring with the furanose ring (X=O).

In one embodiment of the present invention the biradical is —$(CH_2)_{2-4}$—

For these interesting embodiments, it is preferred that the L-ribo-LNA(s) has/have the following general formula Ia.

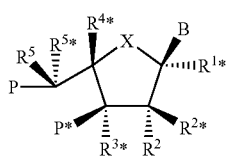

Ia

Also interesting as a separate aspect of the present invention is the variant of formula Ia where B is in the "β-configuration".

The oligomers according to the invention typically comprise 1–10000 L-ribo-LNA(s) of the general formula I (or of the more detailed general formula Ia) and 0–10000 nucleosides selected from naturally occurring nucleosides and nucleoside analogues. The sum of the number of nucleosides and the number of L-ribo-LNA(s) (n) is at least 2, preferably at least 3, in particular at least 5, especially at least 7, such as in the range of 2–15000, preferably in the range of 2–100, such as 3–100, in particular in the range of 2–50, such as 3–50 or 5–50 or 7–50.

It has been found that partly L-ribo-LNA modified oligomers hybridise strongly (with increasing affinity) to DNA and RNA. It is presently believed that fully L-ribo-LNA modified oligomers and oligomers consisting of L-ribo-LNA monomers together with other L-ribo-configurated nucleotide analogues, will give rise to comparable hybridisation properties.

In the present context, the term "nucleoside" means a glycoside of a heterocyclic base. The term "nucleoside" is used broadly as to include non-naturally occurring nucleosides, naturally occurring nucleosides as well as other nucleoside analogues.

Illustrative examples of nucleosides are ribonucleosides comprising a ribose moiety as well as deoxyribonuclesides comprising a deoxyribose moiety. With respect to the bases of such nucleosides, it should be understood that this may be any of the naturally occurring bases, e.g. adenine, guanine, cytosine, thymine, and uracil, as well as any modified variants thereof or any possible unnatural bases.

When considering the definitions and the known nucleosides (naturally occurring and non-naturally occurring) and nucleoside analogues (including known bi- and tricyclic analogues), it is clear that an oligomer may comprise one or more L-ribo-LNA(s) (which may be identical or different both with respect to the selection of substituent and with respect to selection of biradical) and one or more nucleosides and/or nucleoside analogues. In the present context "oligonucleotide" means a successive chain of nucleosides connected via internucleoside linkages, however, it should be understood that a nucleobase in one or more nucleotide units (monomers) in an oligomer (oligonucleotide) may have been modified with a substituent B as defined above.

The oligomers may be linear, branched or cyclic. In the case of a branched oligomer, the branching points may be located in a nucleoside, in an internucleoside linkage or, in an intriguing embodiment, in an L-ribo-LNA. It is believed that in the latter case, the substituents $R^2$, and $R^{3*}$ may designate a group P* designating an internucleoside linkage to a preceding monomer, in particular, $R^2$ designate a further P*.

As mentioned above, the L-ribo-LNA(s) of an oligomer are connected with other monomers via an internucleoside linkage. In the present context, the term "internucleoside linkage" means a linkage consisting of 2 to 4, preferably 3, groups/atoms selected from —$CH_2$—, —O—, —S—, —$NR^H$—, >C=O , >C=$NR^H$, >C=S, —$Si(R^H)_2$—, —SO—, —$S(O)_2$—, —$P(O)_2$—, —$PO(BH_3)$—, —$P(O,S)$—, —$P(S)_2$—, —$PO(R^H)$—, —$PO(OCH_3)$—, and —$PO(NHR^H)$—, where $R^H$ is selected form hydrogen and $C_{1-4}$-alkyl, and $R^H$ is selected from $C_{1-6}$-alkyl and phenyl. Illustrative examples of such internucleoside linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$CH= (including $R^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, —O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—$S(O)_2$—O—, —O—S—$(O)_2$—$CH_2$—, —O—$S(O)_2$—$NR^H$—, —$NR^H$—$S(O)_2$—$CH_2$—, —O—$S(O)_2$—$CH_2$—, —O—$P(O)_2$—O—, —O—$P(O,S)$—O—, —O—$P(S)_2$—O—, —S—$P(O)_2$—O—, —S—$P(O,S)$—O—, —S—$P(S)_2$—O—, —O—$P(O)_2$—S—, —O—$P(O,S)$—S—, —O—$P(S)_2$—S—, —S—$P(O)_2$—S—, —S—$P(O,S)$—S—, —S—$P(S)_2$—S—, —O—$PO(R^H)$—O—, —O—$PO(OCH_3)$—O—, —O—$PO(OCH_2CH_3)$—O—, —O—$PO(OCH_2CH_2S—R)$—O—, —O—$PO(BH_3)$—O—, —O—PO(NHR$^N$)—O—, —O—P(O)$_2$—NR$^H$—, —NR$^H$—P(O)$_2$—O—, —O—P(O,NR$^H$)—O—, —CH$_2$—P(O)$_2$—O—, —O—P(O)$_2$—CH$_2$—, and —O—Si(R$^H$)$_2$—O—; among which —CH$_2$—CO—NR$^H$—, —CH$_2$—NR$^H$—O—, —S—CH$_2$—O—, —O—P(O)$_2$—O—, —O—P(O,S)—O—, —O—P(S)$_2$—O—, —NR$^H$—P(O)$_2$—O—, —O—P(O,NR$^H$)—O—, —O—PO(R$^H$)—O—, —O—PO(CH$_3$)—O—, and —O—PO(NHR$^N$)—O—, where R$^H$ is selected form hydrogen and C$_{1-4}$-alkyl, and R" is selected from C$_{1-6}$-alkyl and phenyl, are especially preferred. Further illustrative examples are given in Mesmaeker et. al., Current Opinion in Structural Biology 1995. 5. 343–355. The left-hand side of the internucleoside linkage is bound to the 5-membered ring as substituent P*, whereas the right-hand side is bound to the 5'-position of a preceding monomer.

It is also clear from the above that the group P may also designate a 5'-terminal group in the case where the L-ribo-LNA in question is the 5'-terminal monomer. Examples of such 5'-terminal groups are hydrogen, hydroxy, optionally substituted C$_{1-6}$-alkyl, optionally substituted C$_{1-6}$-alkoxy, optionally substituted C$_{1-6}$-alkylcarbonyloxy, optionally substituted aryloxy, monophosphate, diphosphate, triphosphate, and —W-A', wherein W is selected from —O—, —S—, and —N(R$^H$)— where R$^H$ is selected from hydrogen and C$_{1-6}$-alkyl, and where A' is selected from DNA intercalators, photochemically active groups, thermochemically active groups, chelating groups, reporter groups, and ligands (where the latter groups may include a spacer as defined for the substituent B).

In the present description and claims, the terms "monophosphate", "diphosphate", and "triphosphate" mean groups of the formula: —O—P(O)$_2$—O, —O—P(O)$_2$—O—P(O)$_2$—O—, and —O—P(O)$_2$—O—P(O)$_2$—O—P(O)$_2$—O—, respectively.

In a particularly interesting embodiment, the group P designates a 5'-terminal groups selected from monophosphate, diphosphate and triphosphate. Especially the triphosphate variant of formula II is interesting as a substrate, such as for enzymes especially for those active on nucleic acids.

Analogously, the group P* may designate a 3'-terminal group in the case where the L-ribo-LNA in question is the 3'-terminal monomer. Examples of such 3'-terminal groups are hydrogen, hydroxy, optionally substituted C$_{1-6}$-alkoxy, optionally substituted C$_{1-6}$-alkylcarbonyloxy, optionally substituted aryloxy, and —W-A', wherein W is selected from —O—, —S—, and —N(R$^H$)— where R$^H$ is selected from hydrogen and C$_{1-6}$-alkyl, and where A'is selected from DNA intercalators, photochemically active groups, thermochemically active groups, chelating groups, reporter groups, and ligands (where the latter groups may include a spacer as defined for the substituent B).

In a preferred embodiment of the present invention, the oligomer has the following formula III:

wherein q is 1–50;

each of n(0), . . . , n(q) is independently 0–10000;

each of m(1), . . . , m(q) is independently 1–10000;

with the proviso that the sum of n(0), . . . , n(q) and m(1), . . . , m(q) is 2–15000;

G designates a 5'-terminal group;

each Nu independently designates a nucleoside selected from naturally occurring nucleosides and nucleoside analogues;

each L-ribo-LNA independently designates a nucleoside analogue;

each L independently designates an internucleoside linkage between two groups selected from Nu and L-ribo-LNA, or L together with G* designates a 3'-terminal group; and each (L-ribo-LNA)-L independently designates a nucleoside analogue of the general formula I as defined above, or preferably of the general formula Ia as defined above.

Within this embodiment, as well as generally, the present invention provides the intriguing possibility of including L-ribo-LNAs with different nucleobases, in particular both nucleobases selected from thymine, cytosine and uracil and nucleobases selected from adenine and guanine. The oligomer may comprise, in one embodiment, at least one L-ribo-LNA wherein B (in formula I or Ia) is selected from the group comprising adenine and guanine and at least one L-ribo-LNA wherein B is selected from the group comprising thymine, cytosine and uracil.

Apart from the oligomers defined above, the present invention also provides monomeric L-ribo-LNAs useful, e.g., in the preparation of oligomers, as substrates for, e.g., nucleic acid polymerases, polynucleotide kinases, terminal transferases, and as therapeutical agents, see further below. The monomeric L-ribo-LNAs correspond in the overall structure (especally with respect to the possible biradicals) to the L-ribo-LNAs defined as constituents in oligomers, however with respect to the groups P and P*, the monomeric L-ribo-LNAs differ slightly as will be explained below. Furthermore, the monomeric L-ribo-LNAs may comprise functional group protecting groups, especially in the cases where the monomeric L-ribo-LNAs are to be incorporated into oligomers by chemical synthesis.

The invention furthermore relates to monomeric L-ribo-LNA nucleosides (L-ribo-LNAs) of the general formula II:

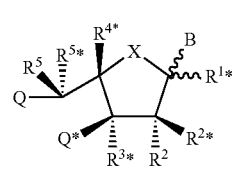

wherein the substituent B is selected from nucleobases, DNA intercalators, photochemically active groups, thermochemically active groups, chelating groups, reporter groups, and ligands; X is selected from —O—, —S—, —N(R$^{N*}$)—, and —C(R$^6$R$^{6*}$)—, preferably from —O—, —S—, and —N(R$^{N*}$)—;

each of Q and Q' is independently selected from hydrogen, azido, halogen, cyano, nitro, hydroxy, Prot-O—, Act-O—, mercapto, Prot-S—, Act-S—, C$_{1-6}$-alkylthio, amino. Prot-N(R$^H$)—, Act-N(R$^H$)—, mono- or di(C$_{1-6}$-alkyl)amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—CH$_2$—, Act-O—CH$_2$—, aminomethyl, Prot-N(R$^H$)—CH$_2$—, Act-N(R$^H$)—CH$_2$—, carboxymethyl, sulphonomethyl, where Prot is a protection group for —OH, —SH, and —NH(R$^H$), respectively, Act is an activation group for —OH, —SH, and —NH(R$^H$), respectively, and R$^H$ is selected from hydrogen and C$_{1-6}$-alkyl;

R$^{3*}$ and R$^{4*}$ together designate a biradical selected from —O—, —S—, —N(R*)—, —(CR*R*)$_{r+s+1}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR*R*)$_{r+s}$—N(R*)—, —N(R*)—(CR*R*)$_{r+s}$—S—, and —S—(CR*R*)$_{r+s}$—N(R*)—; wherein R* is as defined above for the oligomers; and each of the substituents R$^{1*}$, R$^2$, R$^{3*}$, R$^5$, and R$^{5*}$, which are not involved in Q, or Q*, are as defined above for the oligomers.

The monomeric L-ribo-LNAs also comprise basic salts and acid addition salts thereof.

Furthermore, it should be understood that any chemical group (including any nucleobase), which is reactive under the conditions prevailing in chemical oligonucleotide synthesis. is optionally functional group protected as known in the art. This means that groups such as hydroxy, amino, carboxy, sulphono, and mercapto groups, as well as nucleobases, of a monomeric L-ribo-LNA are optionally functional group protected. Protection (and deprotection) is performed by methods known to the person skilled in the art (see, e.g., Greene, T. W. and Wuts, P. G. M., "Protective Groups in Organic Synthesis", 2$^{nd}$ ed., John Wiley, N.Y. (1991), and M. J. Gait, Oligonucleotide Synthesis, IRL Press, 1984).

Illustrative examples of hydroxy protection groups are optionally substituted trityl (Tr), such as 4,4'-dimethoxytrityl (DMT), 4-monomethoxytrityl (MMT), and trityl, optionally substituted 9-(9-phenyl)xanthenyl (pixyl), optionally substituted ethoxycarbonyloxy, p-phenylazophenyloxycarbonyloxy, tetrahydropyranyl (thp), 9-fluorenylmethoxycarbonyl (Fmoc), methoxytetrahydropyranyl (mthp), silyloxy such as trimethylsilyl (TMS), triisopropylsilyl (TIPS), tert-butyldimethylsilyl (TBDMS), triethylsilyl (TES), and phenyldimethylsilyl, benzyloxycarbonyl or substituted benzyloxycarbonyl ethers such as 2-bromo benzyloxycarbonyl, tert-butylethers, alkyl ethers such as methyl ether, acetals (including two hydroxy groups), acyloxy such as acetyl or halogen substituted acetyls, e.g. chloroacetyl or fluoroacetyl, isobutyryl, pivaloyl, benzoyl and substituted benzoyl, methoxymethyl (MOM), benzyl ethers or substituted benzyl ethers such as 2,6-dichlorobenzyl (2,6-Cl$_2$Bzl). Alternatively, the hydroxy group may be protected by attachment to a solid support optionally through a linker.

Illustrative examples of amino protection groups are Fmoc (fluorenylmethoxycarbonyl), BOC (tert-butyloxycarbonyl), trifluoroacetyl, allyloxycarbonyl (alloc, AOC), benzyloxycarbonyl (Z, Cbz), substituted benzyloxycarbonyls such as 2-Chloro benzyloxycarbonyl ((2-ClZ), monomethoxytrityl (MMT), dimethoxytrityl (DMT), phthaloyl, and 9-(9-phenyl)xanthenyl(pixyl).

Illustrative examples of carboxy protection groups are allyl esters, methyl esters, ethyl esters, 2-cyanoethylesters, trimethylsilylethylesters, benzyl esters (Obzl), 2-adamantyl esters (O-2-Ada), cyclohexyl esters (OcHex), 1,3-oxazolines, oxazoler, 1,3-oxazolidines, amides or hydrazides.

Illustrative examples of mercapto protecting groups are trityl (Tr), acetamidomethyl (acm), trimethylacetamidomethyl (Tacm), 2,4,6-trimethoxybenzyl (Tmob), tert-butylsulfenyl (StBu), 9-fluorenylmethyl (Fm), 3-nitro-2-pyridinesulfenyl (Npys), and 4-methylbenzyl (Meb).

Furthermore, it may be necessary or desirable to protect any nucleobase included in a monomeric L-ribo-LNA, especially when the monomeric L-ribo-LNA is to be incorporated in an oligomer according to the invention. In the present context, the term "protected nucleobases" means that the nucleobase in question is carrying a protection group selected among the groups which are well-known for a man skilled in the art (see e.g. Protocols for Oligonucleotides and Analogs, vol 20, (Sudhir Agrawal, ed.), Humana Press, 1993, Totowa, N.J.; S. L. Beaucage and R. P. Iyer, *Tetrahedron*, 1993, 49, 6123; S. L. Beaucage and R. P. Iyer, *Tetrahedron*, 1992. 48, 2223; and E. Uhlmann and A. Peyman, *Chem. Rev.*, 90, 543.). Illustrative examples are benzoyl, isobutyryl, tert-butyl, tert-butyloxycarbonyl, 4-Chloro-benzyloxycarbonyl, 9-fluorenylmethyl, 9-fluorenylmethyloxycarbonyl, 4-methoxybenzoyl, 4-methoxytriphenylmethyl, optionally substituted triazolo, p-toluenesulphonyl, optionally substituted sulphonyl, isopropyl, optionally substituted amidines, optionally substituted trityl, phenoxyacetyl, optionally substituted acyl, pixyl, tetrahydropyranyl, optionally substituted silyl ethers, and 4-methoxybenzyloxyrarbonyl. Chapter 1 in "Protocols for oligonucleotide conjugates", Methods in Molecular Biology, vol 26, (Sudhir Agrawal, ed.), Humana Press, 1993, Totowa, N.J. and S. L. Beaucage and R. P. Iyer, *Tetrahedron*, 1992, 48, 2223 disclose further suitable examples.

In a preferred embodiment, the group B in a monomeric L-ribo-LNA is preferably selected from nucleobases and protected nucleobases.

In an embodiment of the monomeric L-ribo-LNAs according to the present invention, one of Q and Q*, preferably Q*, designates a group selected from Act-O—, Act-S—, Act-N(R$^H$)—, Act-O—CH$_2$—, Act-S—CH$_2$—, Act-N(R$^H$)—CH$_2$—, and the other of Q and Q*, preferably Q, designates a group selected from hydrogen, azido, halogen, cyano, nitro, hydroxy, Prot-O—, mercapto, Prot-S—, C$_{1-6}$-alkylthio, amino, Prot-N(R$^H$)—, mono- or di(C$_{1-6}$-alkyl)amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—CH$_2$—, aminomethyl, Prot-N(R$^H$)—CH$_2$—, carboxymethyl, sulphonomethyl, and R$^H$ is selected from hydrogen and C$_{1-6}$-alkyl.

In the case described above, the group Prot designates a protecting group for —OH, —SH, and —NH(R$^H$), respectively. Such protection groups are selected from the same as defined above for hydroxy protection groups, mercapto protection group, and amino protection groups, respectively, however taking into consideration the need for a stable and reversible protection group. However, it is preferred that any protection group for —OH is selected from optionally substituted trityl, such as dimethoxytrityl (DMT), monomethoxytrityl (MMT), and trityl, and 9-(9-phenyl) xanthenyl (pixyl), optionally substituted, tetrahydropyranyl (thp) (further suitable hydroxy protection groups for phosphoramidite oligonucleotide synthesis are described in Agrawal, ed. "Protocols for Oligonucleotide Conjugates"; Methods in Molecular Biology, vol. 26, Humana Press, Totowa, N.J. (1994) and Protocols for Oligonucleotides and Analogs, vol 20, (Sudhir Agrawal, ed.), Humana Press, 1993, Totowa, N.J.), or protected as acetal; that any protection group for —SH is selected from trityl, such as dimethoxytrityl (DMT), monomethoxytrityl (MMT), and trityl, and 9-(9-phenyl)xanthenyl (pixyl), optionally substituted, tetrahydropyranyl (thp) (further suitable mercapto protection groups for phosphoramidite oligonucleotide synthesis are also described in Agrawal (see above): and that any protecting group for —NH($R^H$) is selected from trityl, such as dimethoxytrityl (DMT), monomethoxytrityl (MMT), and trityl, and 9-(9-phenyl)xanthenyl (pixyl), optionally substituted, tetrahydropyranyl (thp) (further suitable amino protection groups for phosphoramidite oligonucleotide synthesis are also described by Agrawal (see above).

In the embodiment above, as well as for any monomeric L-ribo-LNAs defined herein, Act designates an activation group for —OH, —SH, and —NH($R^H$), respectively. Such activation groups are, e.g., selected from optionally substituted O-phosphoramidite, optionally substituted O-phosphortriester, optionally substituted O-phosphordiester, optionally substituted H-phosphonate, and optionally substituted O-phosphonate.

In the present context, the term "phosphoramidite" means a group of the formula —P($OR^x$)—N($R^y$)$_2$, wherein $R^x$ designates an optionally substituted alkyl group, e.g. methyl, 2-cyanoethyl, or benzyl, and each of $R^y$ designate optionally substituted alkyl groups, e.g. ethyl or isopropyl, or the group —N($R^y$)$_2$ forms a morpholino group (—N(CH$_2$CH$_2$)$_2$O). $R^x$ preferably designates 2-cyanoethyl and the two $R^y$ are preferably identical and designate isopropyl. Thus, an especially relevant phosphoramidite is N,N-diisopropyl-O-(2-cyanoethyl)phosphoramidite.

It should be understood that the protecting groups used herein for a single monomeric L-ribo-LNA or several monomeric L-ribo-LNAs may be selected so that when this/these L-ribo-LNA(s) are incorporated in an oligomer according to the invention, it will be possible to perform either a simultaneous deprotection or a sequential deprotection of the functional groups. The latter situation opens for the possibility of regioselectively introducing one or several "active/functional" groups such as DNA intercalators, photochemically active groups, thermochemically active groups, chelating groups, reporter groups, and ligands, where such groups may be attached via a spacer as described above.

In a preferred embodiment, Q is selected from hydrogen, azido, halogen, cyano, nitro, hydroxy, Prot-O—, mercapto, Prot-S—, $C_{1-6}$-alkylthio, amino, Prot-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate, diphosphate, triphosphate, DNA intercalators, photochemically active groups, thermochemically active groups, chelating groups, reporter groups, ligands, carboxy, sulphono, hydroxymethyl, Prot-O—CH$_2$—, aminomethyl, Prot-N($R^H$)—CH$_2$—, carboxymethyl, sulphonomethyl, where Prot is a protection group for —OH, —SH, and —NH($R^H$), respectively, and $R^H$ is selected from hydrogen and $C_{1-6}$-alkyl; and Q* is selected from hydrogen, azido, halogen, cyano, nitro, hydroxy, Act-O—, mercapto, Act-S—, $C_{1-6}$-alkylthio, amino, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, DNA intercalators, photochemically active groups, thermochemically active groups, chelating groups, reporter groups, ligands, carboxy, sulphono, where Act is an activation group for —OH, —SH, and —NH($R^H$), respectively, and $R^H$ is selected from hydrogen and $C_{1-6}$-alkyl.

The monomeric L-ribo-LNAs of the general formula II may, as the L-ribo-LNAs incorporated into oligomers, represent various stereoisomers. Thus, the stereochemical variants described above for the L-ribo-LNAs incorporated into oligomers are believed to be equally applicable in the case of monomeric L-ribo-LNAs (however, it should be noted that P should then be replaced with Q).

In a preferred embodiment of the present invention, the monomeric LNA has the general formula IIa

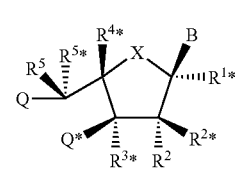

IIa wherein the substituents are defined as above.

Furthermore, with respect to the definitions of substituents, biradicals, R*, etc. the same preferred embodiments as defined above for the oligomer according to the invention also apply in the case of monomeric L-ribo-LNAs.

In a particularly interesting embodiment of the monomeric L-ribo-LNAs of the present invention, B designates a nucleobase, preferably a nucleobase selected from thymine, cytosine, uracil, adenine and guanine (in particular adenine and guanine), X is —O—, $R^{2*}$ and $R^{4*}$ together designate a biradical selected from —(CH$_2$)$_{0-1}$—O—(CH$_2$)$_{1-3}$—, —(CH$_2$)$_{0-1}$—S—(CH$_2$)$_{1-3}$—, and —(CH$_2$)$_{0-1}$—N($R^N$)—(CH$_2$)$_{1-3}$—, in particular —O—CH$_2$—, —S—CH$_2$— and —$R^N$—CH$_2$—, where $R^N$ is selected from hydrogen and $C_{1-4}$-alkyl, Q designates Prot-O—, Q* designates Act-OH, and $R^{1*}$, $R^2$, $R^{3*}$, $R^5$, and $R^{5*}$ each designate hydrogen. In this embodiment, $R^N$ may also be selected from DNA intercalators, photochemically active groups, thermochemically active groups, chelating groups, reporter groups and ligands.

In a further particularly interesting embodiment of the monomeric L-ribo-LNAs of the present invention, B designates a nucleobase, preferably a nucleobase selected from thymine, cytosine, uracil, adenine and guanine (in particular adenine and guanine), X is —O—, $R^{2*}$ and $R^{4*}$ together designate a biradical selected from —(CH$_2$)$_{0-1}$—O—(CH$_2$)$_{1-3}$—, —(CH$_2$)$_{0-1}$—S—(CH$_2$)$_{1-3}$—, and —(CH$_2$)$_{0-1}$—N($R^N$)—(CH$_2$)$_{1-3}$—, in particular —O—CH$_2$—, —S—CH$_2$— and —$R^N$—CH$_2$—, where $R^N$ is selected from hydrogen and $C_{1-4}$-alkyl, Q is selected from hydroxy, mercapto, $C_{1-6}$-alkylthio, amino, mono- or di($C_{1-6}$-alkyl)amino, optionally substituted $C_{1-6}$-alkoxy, optionally substituted $C_{2-6}$-alkenyloxy, optionally substituted $C_{2-6}$-alkynyloxy, monophosphate, diphosphate, and triphospnate, Q* is selected from hydrogen, azido, halogen, cyano, nitro, hydroxy, mercapto, $C_{1-6}$-alkylthio, amino, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, and optionally substituted $C_{2-6}$-alkynyloxy, $R^{3*}$ is selected from hydrogen, optionally substituted $C_{1-6}$-alkyl, optionally substituted $C_{2-6}$-alkenyl, and optionally substituted $C_{2-6}$-alkynyl, and $R^{1*}$, $R^2$, $R^5$, and $R^{5*}$ each designate hydrogen Also here, $R^N$ may also be selected from DNA intercalators, photochemically active groups, thermochemically active groups, chelating groups, reporter groups and ligands.

One aspect of the invention is to provide various derivatives of L-ribo-LNAs for solid-phase and/or solution phase incorporation into an oligomer. As an illustrative example, monomers suitable for incorporation of (1R,3R,4S,7R)-7-hydroxy-1-hydroxymethyl-3-(thymin-1-yl)-2,5-dioxabicyclo[2.2.1]heptane, (1R,3R,4S,7R)-7-hydroxy-1-hydroxymethyl-3-(cytosin-1-yl)-2,5-dioxabicyclo[2.2.1]heptane, (1R,3R,4S,7R)-7-hydroxy-1-hydroxymethyl-3-(uracil-1-yl)-2,5-dioxabicycio[2.2.1]heptane, (1R,3R,4S,7R)-7-hydroxy-1-hydroxymethyl-3-(guanin-1-yl)-2,5-dioxabicyclo[2.2.1]heptane, and (1R,3R,4S,7R)-7-hydroxy-1-hydroxymethyl-3-(adenin-1-yl)-2,5-dioxabicyclo[2.2.1]heptane using the phsphoramidite approach, the phosphortriester approach, and the H-phosphonate approach, respectively, are (1R,3R,4S,7R)-7-(2-Cyanoethoxy(diisopropyl-amino) phosphinoxy)-1-(4,4'-dimethoxytrityloxymethyl)-3-(thymin-1-yl)-2,5-dioxabicyclo[2.2.1]heptane, (1R,3R,4S,7R)-7-hydroxy-1-(4,4'-dimethoxytrityloxymethyl)-3-(thymin-1-yl)-2,5-dioxabicyclo[2.2.1]heptane-7-O-(2-Chlorophenylphosphate), and (1R,3R,4S,7R)-7-hydroxy-1-(4,4'-dimethoxytrityloxymethyl)-3-(thymin-1-yl)-2,5-dioxabicyclo[2.2.1]heptane-7—O—(H-phosphonate) and the 3-(cytosin-1-yl), 3-(uracil-1-yl), 3-(adenin-1-yl) and 3-(guanin-1-yl) analogues thereof, respectively. Furthermore, the analogues where the methyleneoxy biradical of the monomers is substituted with a methylenethio, a methyleneamino, or a 1,2-ethylene biradical are also expected to constitute particularly interesting variants within the present invention. The methylenethio and methyleneamino analogues are believed to equally applicable as the methyleneoxy analogue and therefore the specific reagents corresponding to those mentioned for incorporation of (1R,3R,4S,7R)-7-hydroxy-1-hydroxymethyl-3-(thymin-1-yl)-2,5-dioxabicyclo[2.2.1]heptane, (1R,3R,4S,7R)-7-hydroxy-1-hydroxymethyl-3-(cytosin-1-yl)-2,5-dioxabicyclo[2.2.1]heptane, (1R,3R,4S,7R)-7-hydroxy-1-hydroxymethyl-3-(uracil-1-yl)-2,5-dioxabicyclo[2.2.1]heptane, (1R,3R,4S,7R)-7-hydroxy-1-hydroxymethyl-3-(guanin-1-yl)-2,5-dioxabicyclo[2.2.1]heptane, and (1R,3R,4S,7R)-7-hydroxy-1-hydroxymethyl-3-(adenin-1-yl)-2,5-dioxabicyclo[2.2.1]heptane should also be considered as particularly interesting reactive monomers within the present invention. For the methyleneamine analogue, it should be noted that the secondary amine may carry a substituent selected from optionally substituted $C_{1-6}$-alkyl such as methyl and benzyl, optionally substituted $C_{1-6}$-alkylcarbonyl such as trifluoroacetyl, optionally substituted arylcarbonyl and optionally substituted heteroarylcarbonyl.

Also interesting as a separate aspect of the present invention is the variant of formula II or IIa where B is in the "β-configuration".

Preparation of Monomers

In a preferred embodiment, α-L-ribo-LNA containing a 2'-O,4'-C-methylene bridge was synthesised by the following procedure: Benzoylation of 4-C-hydroxymethyl-α-D-xylofuranose 1 (T. F. Tam and B. Fraser-Ried, *Can. J. Chem.*, 1979, 57, 2818) afforded the di-O-benzoyl derivative 2 which was subsequently converted into the 1,2-di-O-acetylated furanose 3 by acetolysis using 80% acetic acid followed by acetylation. Employing a modified Vorbrüggen methodology (H. Vorbrüggen, K. Krolikiewicz and B Bennua, *Chem. Ber.*, 1981, 114, 1234; H. Vorbrüggen and G. Höfle, *Chem. Ber.*, 1981, 114, 1256), the thymine β-configured nucleoside 4 was stereoselectively obtained by in situ silylation of thymine and trimethylsilyl triflate mediated coupling. Treatment of compound 4 with sodium methoxide resulted in deacylation to give nucleoside triol 5. 4,4'-Dimethoxytrityl protection followed by tosylation afforded the 5'-O-4,4'-dimethoxytrityl protected nucleoside derivative 7. Base-induced ring closure afforded the bicyclic nucleoside derivative 8. Debenzylation yielded the bicyclic nucleoside analogue 9 which was transformed into the phosphoramidite derivative 10 for oligonucleotide synthesis. The coupling method used in the example is only one of several possible methods as will be apparent for a person skilled in the art.

Figure 2:
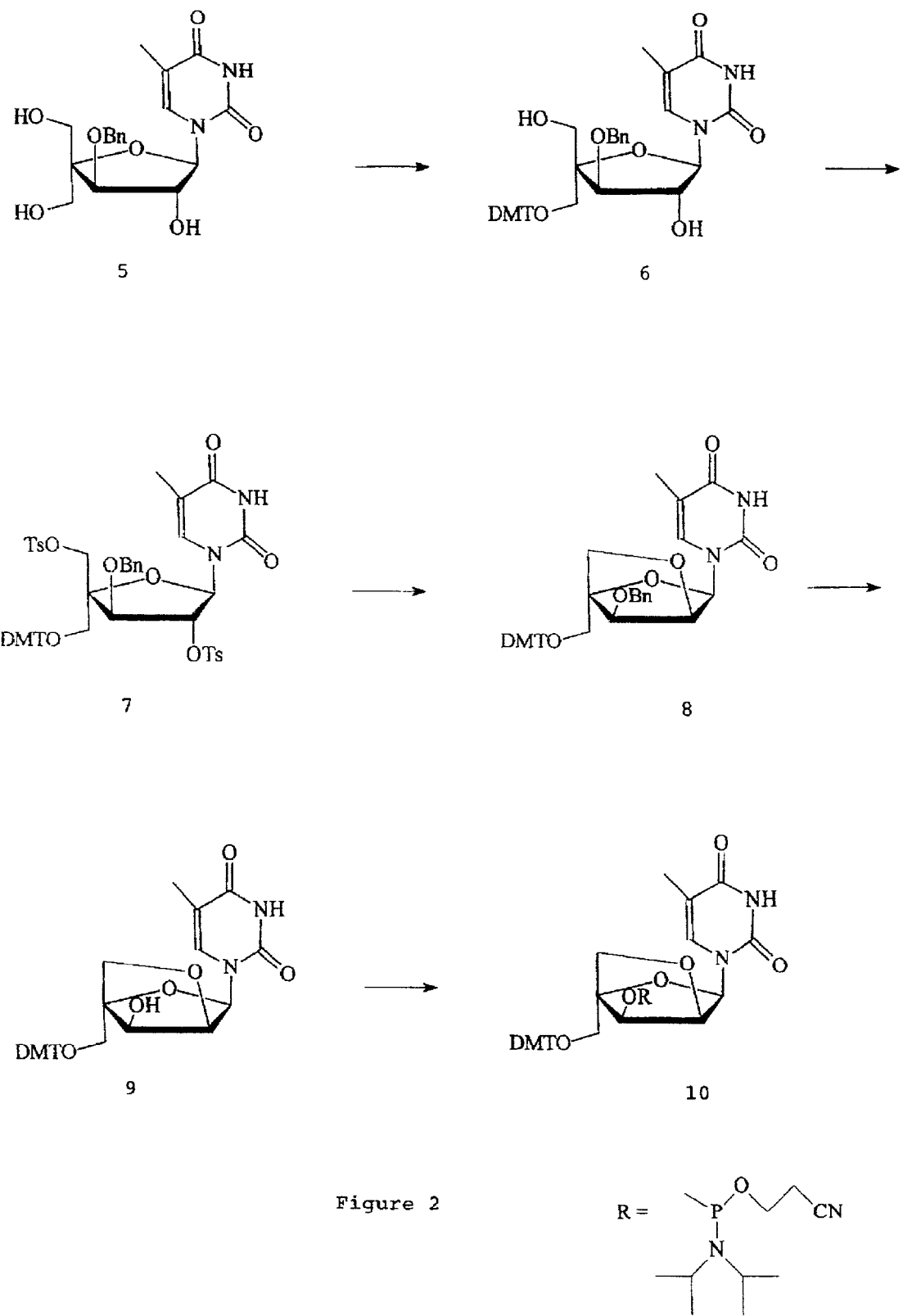
FIG. 2 illustrates syntheses of Examples 5–10.
Figure 3:
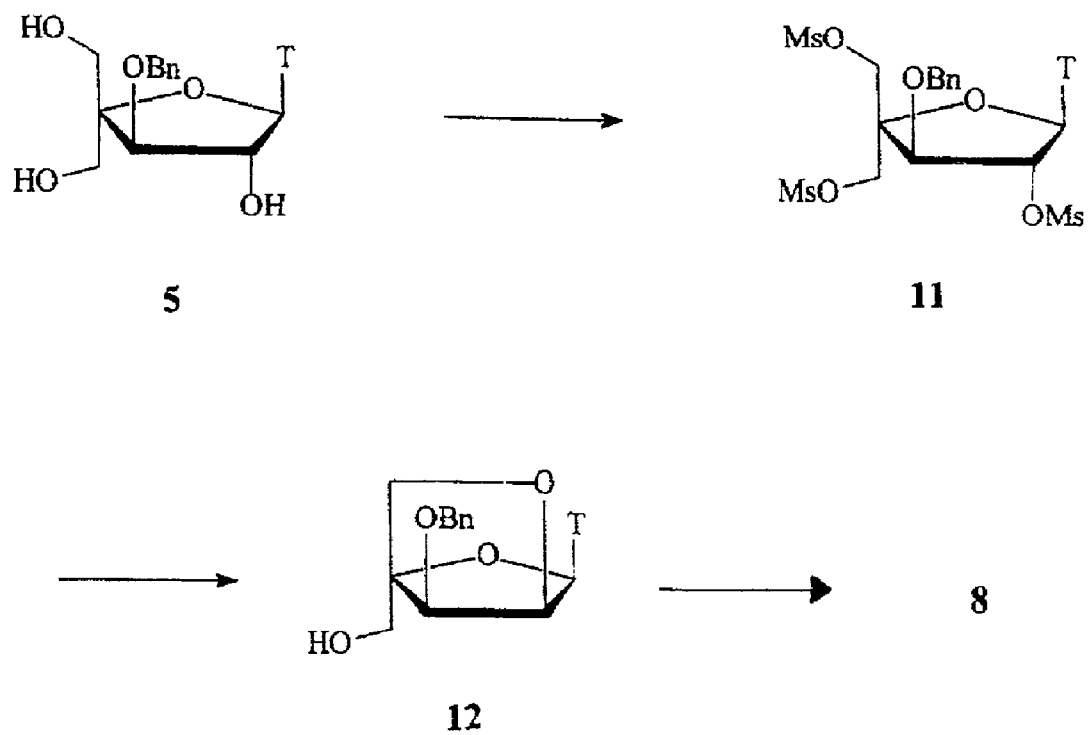
FIG. 3 illustrates syntheses of Examples 12–14.

As an alternative route the synthetic sequence shown in FIG. 3 (Examples 12–14) can be used. Thus, nucleoside 5 was trimesylated to give nucleoside 11 which could be cyclized using NaOH/EtOH/$H_2O$. Under the experimental conditions used, concomitant conversion of the remaining mesyloxy group to an hydroxyl group was observed yielding nucleoside 12. Standard DMT-protection as outlined in example 14 is expected to yield nucleoside 8, a convenient intermediate towards synthesis of the α-L-ribo-LNA nucleoside phosphoramidite derivative 10 (FIG. 2).

The described example is meant to be illustrative for the procedures and examples of this invention. The structures of the synthesised compounds were verified using 1D NMR.

The methods depicted in Schemes 1, 2 and 3 can likewise be used to synthesize α-L-ribo-LNA nucleoside derivatives of other pyrimidine bases than thymine, e.g. uracil, cytosine, 5-substituted uracil, 5-substituted cytosine as well as otherwise substituted pyrimidines. Alternatively, the uracil derivatives can be converted to the corresponding cytosine derivatives, and the thymine derivatives to the corresponding 5-methylcytosine derivatives, using well known methods (Koshkin, A. A., Singh, S. K., Nielsen, P., Rajwanshi, V. K., Kumar, R., Meldgaard, M., Olsen, C. E., Wengel, J. *Tetrahedron* 1998, 54, 3607; Obika, S., Nanbu, D., Hari, Y., Andoh, J., Morio, K., Doi, T., Imanishi, T. *Tetrahedron Lett.* 1998, 39, 5401).

For synthesis of purine α-L-ribo-LNA nucleoside derivatives a number of suitable synthetic methods can be devised. It should be noted that the term "α-face" when mentioned below refers to the α-face of the natural RNA nucleoside monomers, that the term "β-face" when mentioned below refers to the β-face of the natural RNA nucleoside monomers, and that the terms "β-purine nucleoside" or "β-pyrimidine nucleoside" mean that the nucleobases are positioned as in the natural RNA nucleoside monomers. As an example of a possible synthetic route towards the purine α-L-ribo-LNA nucleoside derivatives, cyclization of arabino-configured analogues (2'-OH group positioned at the β-face of the furanose ring) can be utilized. These nucleosides can be prepared from the corresponding arabino-configured parent nucleosides via 5'-oxidation, aldol condensation and reduction.

Protecting group manipulations and activation of the 5'-OH group (positioned at the β-face of the furanose ring) should then prepare for the desired cyclization as mentioned above. Alternatively, 2'-oxidation of the 2'-OH group of 4'-C-hydroxymethyl derivatives of β-purine ribofuranosyl nucleosides (with the 2'-OH and 3'-OH groups positioned at the α-face of the furanose ring and the 3'-OH positioned at the β-face of the furanose ring (or alternatively at the α-face of the furanose ring) with concomitant inversion at C3') followed by stereoselective reduction (using e.g. $NaBH_4$) should furnish the desired nucleoside with inverted configuration at the 2'-carbon atom Protecting group manipulations and activation of the 5'-OH group (positioned at the β-face of the furanose ring) should then prepare for the desired cyclization as mentioned above Other procedures can be anticipated to be useful for inversion of the configuration at the 2'-carbon atom of 4'-C-hydroxymethyl derivatives of β-purine ribofuranosyl nucleosides (with the 2'-OH and 3'-OH groups positioned at the β-face of the furanose ring and the 3'-OH group positioned at the β-face of the furanose ring, or alternatively at the α-face with concomitant inversion at C3', of the furanose ring), e.g. the Mitsunobu reaction or nucleophilic displacement reactions of 2'-O-activated derivatives derivatives (e.g., 2'-O-mesyl, 2'-O-tosyl or 2'-O-trifluoromethanesulfonyl derivatives) with O-nucleophiles like acetate, benzoate, alkoxide or the like Subsequent deprotection to give a 5'-hydroxy-4'-C-hydroxymethyl derivative, activation to prepare for cyclization (e.g., by mono- or dimesylation, mono- or ditosylation, or mono- or ditrifluoromethanesulfonation), cyclization (after deprotection of the 2'-OH group if necessary), and deprotections should furnish she desired purine α-L-ribo nucleosides. It should be noted that the purine bases preferably should be protected in the target monomers and that this can be accomplished during the synthetic route of choice, or as the last step, by trimethylsilylation, protection of the free amino group of the purine bases, and desilylation. The starting 4'-C-hydroxymethyl derivatives of β-purine nucleosides may, in one embodiment, be prepared by coupling of furanose derivative 3 (FIG. 1) with properly protected adenine or guanine derivatives following the known Vorbrüggen type coupling methods (see e.g. synthesis of nucleoside 4; FIG. 1) (Koshkin, A. A., Singh, S. K., Nielsen, P., Rajwanshi, V. K., Kumar, R., Meldgaard, M., Olsen, C. E., Wengel, J. *Tetrahedron* 1998, 54, 3607).

It is anticipated that inversion of the configuration as described above may be performed on natural β-purine ribofuranosyl nucteosides (with the 2'-OH positioned at the α-face of the furanose ring ring and the 3'-OH group positioned at the β-face of the furanose ring, or alternatively at the α-face of the furanose ring with concomitant inversion at C3') with the introduction of the additional 4'-C-hydroxymethyl group to follow thereafter using known procedures, e.g. those described aoove. One may also expect that either enzymatic or chemical transglycosylation reactions on properly derivatized and protected pyrimidine nucleosides, either arabino-configured β-pyrimidine furanosyl nucleosides, arabino-configured 4'-C-hydroxymethyl-β-pyrimidine furanosyl nucleosides, or already cyclized α-L-ribo-LNA pyrimidine nucleosides are possible synthetic routes towards the purine α-L-ribo-LNA nucleoside derivatives. Alternatively, 4-C-hydroxymethylation, inversion of the configuration at the 2-carbon atom, and cyclization, or one of these procedures or two of these procedures (whatever needed depends on the starting material applied) can be performed starting from a furanose or hexose. Subsequently, before or after cyclization, coupling with different bases (purines or pyrimidines—protected if needed) would furnish nucleoside derivatives useful for synthesis of α-L-ribo-LNA pyrimidine and purine nucleosides after the necessary protecting group manipulations and/or OH-group activations. As yet another procedure to synthesize α-L-ribo-LNA pyrimidine or purine nucleosides, direct building-up of the desired nuclebased, in two or more chemical steps) from an appropriately derivatized furanosyl derivative, e.g. furanosyl amine, should be possible.

Figure 4:
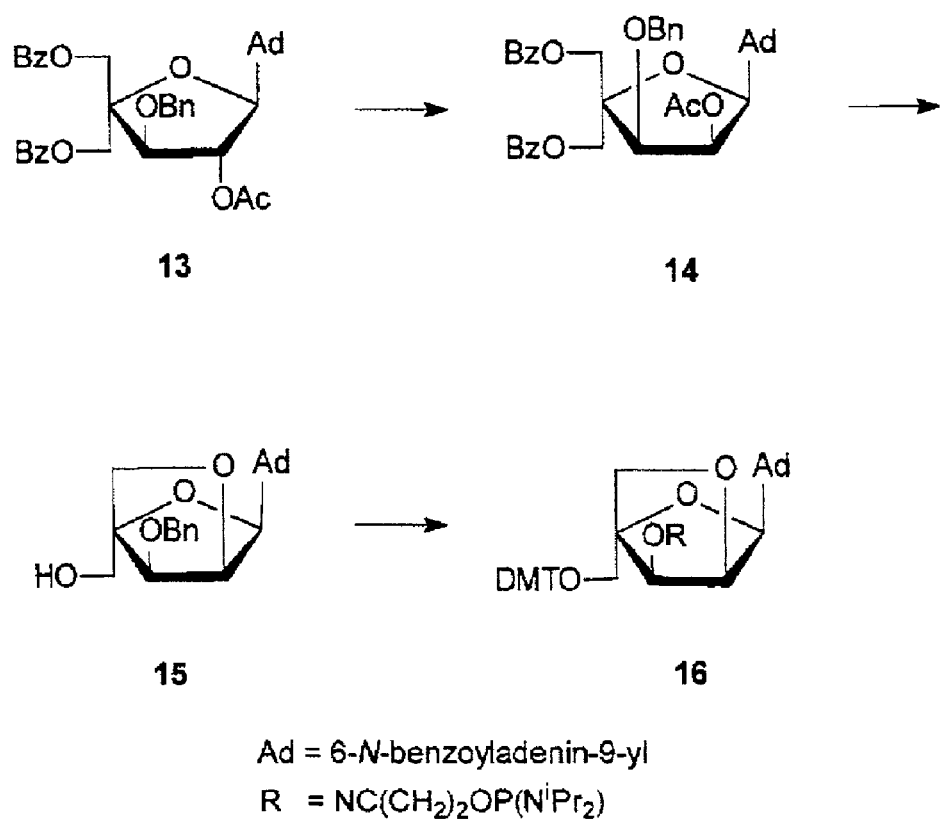
FIG. 4 illustrates syntheses of Examples 15–17.

In a preferred embodiment, the procedures described in examples 15, 16 and 17 (FIG. 4) can be used to prepare the purine α-L-LNA monomers, e.g. the adenine or guanine derivatives. Thus, sugar 3 was coupled with N-6-benzoyladenine to give nucleoside 13 which was selectively deacetylated and subsequently converted into the 2'-O-trifluoromethanesulfonyl derivative. Concomitant reaction with potassium acetate gave the 2'-O-acetyl derivative 14 with inversion at C2' Complete deacylation followed by reprotection of the adenine moiety, selective mesylation of the two primary hydroxyl groups and treatment with sodium hydroxide in water dioxane afforded the α-L-LNA adenine nucleoside 15. DMT-protection of nucleoside 15 followed by debenzylation and 3'-O-phosphitylation (Koshkin, A. A., Singh, S. K., Nielsen, P., Rajwanshi, V. K., Kumar, R., Meldgaard, M., Olsen, C. E., Wengel, J. *Tetrahedron* 1998, 54, 3607) is one possible route to obtain the phosphoramidite derivative 16. Debenzylation of 15 followed by selective DMT-protection of the primary hydroxyl group and 3'-O-phosphitylation is another route affording phosphoramidite derivative 16.

All the methods and procedures described above for synthesis of α-L-ribo-LNA purine nucleosides are also applicable as alternative methods for synthesis of the α-L-ribo-LNA pyrimidine nucleosides.

The methods described above for synthesis of α-L-ribo-LNA pyrimidine and purine nucleosides leads naturally to methods useful for synthesis of 2'-amino and 2'-thio derivatives of α-L-ribo-LNA nucleosides. As one example, cyclization by attack of a 2'-amino or 2'-thio group positioned at the β-face of the furanose ring on a properly activated 5'-OH group should furnish the 2'-amino or 2'-thio α-L-ribo-LNA pyrimidine or purine nucleosides. Alternatively, cyclization by attack of a 5'-amino or 5'-thio group positioned at the 62 -face of the furanose ring on a properly activated 2'-OH group positioned at the α-face of the furanose ring should furnish the 2'-amino or 2'-thio α-L-ribo-LNA pyrimidine or purine nucleosides As yet another method, cyclization of properly activated, protected and configured derivatives, e.g. 2'-O,5'-O-dimesyl, 2'-O,5'-O-ditosyl, or 2'-O,5'-O-ditrifluoromethanesulfonyl nucleosides, using amino or thio nucleophiles (e.g. benzylamine and potassium thioacetate, respectively) should furnish the 2'-amino and 2'-thio derivatives of α-L-LNA nucleosides. Likewise, an attack by a 5'-OH group positioned at the β-face of the furanose ring on a properly activated 2'-OH group group positioned at the α-face of the furanose ring should furnish the parent α-L-ribo-LNA pyrimidine or purine nucleosides.

It is expected that the method used for oligomerization of the α-L-ribo-LNA pyrimidine nucleosides mat be used succesfully also for the α-L-ribo-LNA purine nudeosides. Alternatively, any known method for automated or solution-phase synthesis of oligonucleotides and analogues, e.g. the phophortriester method, the H-phosphonate method or any variant of the phosphoramidite method used for oligomerization of the α-L-ribo-LNA pyrimidine nucleosides, should also be applicable.

Preparation of Oligomers

Linear-, branched- (M. Grøtli and B. S. Sproat, *J. Chem. Soc., Chem. Commun.,* 1995, 495; R. H. E. Hudson and M. J. Damha, *J. Am. Chem. Soc.,* 1993, 115, 2119; M. Von Büren, G. V. Petersen, K. Rasmussen, G. Brandenburg, J. Wengel and F. Kirpekar, *Tetrahedron,* 1995, 51, 8491) and circular- (G. Prakash and E. T Kool, *J. Am. Chem. Soc.,* 1992, 114, 3523) oligo- and polynucleotides of the invention may be produced using the polymerisation techniques of nucleic acid chemistry well known to a person of ordinary skill in the art of organic chemistry. Phosphoramidite chemistry (S. L. Beaucage and R. P. Iyer, *Tetrahedron,* 1993, 49, 6123; S. L. Beaucage and R. P. Iyer, *Tetrahedron,* 1992, 48, 2223) was used, but for instance H-phosphonate chemistry, phosphortriester chemistry or enzymatic synthesis could also be used. The standard coupling conditions for the phosphoramidite approach was slightly modified using pyridine hydrochloride instead of 1H-tetrazole as a highly efficient reagent for activating nucleoside phosphoramidites during oligonucleotide synthesis, and a prolongation of the coupling time to between 10 to 30 min.

After synthesis of the desired sequence, deprotection and cleavage from the solid support (cleavage from solid support and removal of protection groups using concentrated ammonia in methanol at room temperature for 12 h) and subsequent reversed phase purification using commercially available disposable cartridges (which includes detritylation) yield the final oligomeric product. Alternatively, purification of L-ribo-LNA oligonucleotides can be done using disposable reversed phase HPLC and/or precipitation from ethanol or butanol. Capillary gel electrophoresis was used to verify the purity and the composition of the synthesised oligonucleotide analogues however, purity and composition can also be verified using reversed phase HPLC and MALDI-MS.

Generally, the present invention provides the use of L-ribo-LNAs as defined herein for the preparation of L-ribo-LNA modified oligonucleotides. Is should be understood that L-ribo-LNA modified oligonucleotides may comprise normal nucleosides (i.e. naturally occurring nucleosides such as ribonucleosides and/or deoxyribonucleosides), as well as modified nucleosides different from those defined with the general formula II.

Furthermore, solid support materials having immobilised thereto an optionally nucleobase protected and optionally 5'-OH protected LNA are especially interesting as material for the synthesis of LNA modified oligonucleotides where an LNA monomer is included in at the 3'-end. In this instance, the solid support material is preferable CPG, e.g. a readily (commercially) available CPG material onto which a 3'-functionalised, optionally nucleobase protected and optionally 5'-OH protected LNA is linked using the conditions stated by the supplier for that particular material. BioGenex Universal CPG Support (BioGenex, U.S.A.) can e.g. be used. The 5'-OH protecting group may, e.g., be a DMT group. 3'-functional group should be selected with due regard to the conditions applicable for the CPG material in question.

Applications

The present invention discloses the surprising finding that derivatives of L-ribo-LNAs, when incorporated into partly modified oligonucleotides, decrease the affinity of these modified oligonucleotides for both complementary DNA and RNA compared to the unmodified oligonucleotides. However, when incorporated into fully L-ribo-LNA modified oligonucleotides a dramatically increase in hybridisation properties for both complementary ssDNA and ssRNA is observed. The α-L-ribo-LNA—a special variant of the L-ribo-LNAs—in addition to the described properties has an ability to discriminate between RNA and DNA targets when hybridizing. Depending on the application, the use of fully modified L-ribo-LNA oligonucleotides thus offers the intriguing possibility to either greatly increase the affinity of a standard oligonucleotide without compromising specificity (constant size of oligonucleotide), significantly increase the specificity without compromising affinity (reduction in the size of the oligonucleotide) or specifically hybridize to RNA targets.

It is also believed that L-ribo-LNA modified oligonucleotides, in addition to greatly enhanced hybridisation properties, display many of the useful physicochemical properties of normal DNA and RNA oligonucleotides. The prospect includes excellent solubility, a response of LNA modified oligonucleotides to salts like sodium chloride and tetramethylammonium chloride which mimic that of the unmodified oligonucleotides, the ability of LNA modified oligonucleotides to act as primers for a variety of polymerases, the ability of LNA modified nucleotides to act as primers in a target amplification reaction using a thermostable DNA polymerase, the ability of LNA modified oligonucleotides to act as a substrate for T4 polynucleotide kinase, the ability of biotinylated LNAs to sequence specifically capture PCR amplicons onto a streptavidine coated solid surface, the ability of immobilised LNA modified oligonucleotides to sequence specifically capture amplicons and very importantly the ability of LNA modified oligonucleotides to sequence specifically target double-stranded DNA by strand invasion. Hence, it is apparent to one of ordinary skills in the art that these novel nucleoside analogues are extremely useful tools to improve the performance in general of oligonucleotide based techniques in therapeutics, diagnostics and molecular biology.

An object of the present invention is to provide monomeric L-ribo-LNAs according to the invention which can be incorporated into oligonucleotides using procedures and equipment well known to one skilled in the art of oligonucleotide synthesis.

Another object of the present invention is to provide fully or partly L-ribo-LNA modified oligonucleotides (oligomers) that are able to hybridise in a sequence specific manner to complementary oligonucleotides forming either duplexes or triplexes of substantially higher affinity than the corresponding complexes formed by unmodified oligonucleotides.

Another object of the present invention is to use fully L-ribo-LNA modified oligonucleotides to obtain enhanced specificity of the oligonucleotides without compromising on the affinity Another object of the present invention is to provide fully or partly modified oligonucleotides comprising both L-ribo-LNAs, normal nucleosides and other nucleoside analogues.

A further object of the present invention is to exploit the high affinity of L-ribo-LNAs to create fully modified oligonucleotides of extreme affinity that are capable of binding to their target sequences in a dsDNA molecule by way of "strand displacement".

A further object of the invention is to provide different classes of L-ribo-LNAs which, when incorporated into oligonucleotides, differ in their affinity towards their complementary nucleosides. This can be achieved for example by substituting the normal nucleobases G, A, T, C and U with derivatives having, for example, altered hydrogen bonding possibilities.

Another object of the present invention is to provide L-ribo-LNA modified oligonucleotides which are more resistant to nucleases than their unmodified counterparts.

Another object of the present invention is to provide L-ribo-LNA modified oligonucleotides which can discriminate between DNA and RNA targets when hybridizing. It has surprisingly been shown by $T_m$ measurements that the $T_m$ of α-L-ribo-LNA against complementary RNA oligonucleotides is increased 5.7° C. per modification compared to only 2.7° C. per modification against complementary DNA (as shown in example 11, Table 3) α-L-ribo-LNA oligos will thus have an increased affinity towards RNA compared to DNA allowing conditions to be created under which α-L-ribo-LNA specifically will hybridize to a given RNA but not to a DNA having the same base sequence. This ability to discriminate between RNA and DNA can be exploited in a number of situations described below.

Another object of the present invention is to provide L-ribo-LNA modified oligonucleotides which can recruit RNAseH.

An additional object of the present invention is to provide L-ribo-LNAs that can act as substrates for DNA and RNA polymerases thereby allowing the analogues to be either incorporated into a growing nucleic acid chain or to act as chain terminators.

A further object of the present invention is to provide L-ribo-LNAs that can act as therapeutic agents. Many examples of therapeutic nucleoside analogues are known and similar derivatives of the nucleoside analogues disclosed herein can be synthesised using the procedures known from the literature (E. De Ciercq, *J. Med. Chem.* 1995, 38, 2491; P. Herdewijn and E. De Clercq: Classical Antiviral Agents and Design of New Antiviral Agents. In: A Textbook of Drug Design and Development; Eds. P. Krogsgaard-Larsen, T. Liljefors and U. Madsen; Harwood Academic Publishers, Amsterdam, 1996, p. 425; I. K. Larsen: Anticancer Agents. In: A Textbook of Drug Design and Development; Eds. P. Krogsgaard-Larsen, T. Liljefors and U. Madsen; Harwood Academic Publishers, Amsterdam, 1996, p. 460).

Double-stranded RNA has been demonstrated to posses anti-viral activity and tumour suppressing activity (Sharp et al., *Eur. J. Biochem.* 230(1): 97–103, 1995, Lengyel-P. et al., *Proc. Natl. Acad. Sci. U.S.A.,* 90(13): 5893–5, 1993, and Laurent-Crawford et al., *AIDS Res. Hum. Retroviruses,* 8(2): 285–90, 1992). It is likely that double stranded LNAs may mimic the effect of therapeutically active double stranded RNAs and accordingly such double stranded LNAs have a potential as therapeutic drugs.

When used herein, the term "natural nucleic acid" refers to nucleic acids in the broadest sense, like for instance nucleic acids present in intact cells of any origin or vira or nucleic acids released from such sources by chemical or physical means or nucleic acids derived from such primary sources by way of amplification. The natural nucleic acid may be single, double or partly double stranded, and may be a relatively pure species or a mixture of different nucleic acids. It may also be a component of a crude biological sample comprising other nucleic acids and other cellular components. On the other hand, the term "synthetic nucleic acids" refers to any nucleic acid produced by chemical synthesis.

The present invention also provides the use of L-ribo-LNA modified oligonucleotides in nucleic acid based therapeutic, diagnostics and molecular biology. The L-ribo-LNA modified oligonucleotides can be used in the detection, identification, capture, characterisation, quantification and fragmentation of natural or synthetic nucleic acids. and as blocking agents for translation and transcription in vivo and in vitro. In many cases it will be of interest to attach various molecules to L-ribo-LNA modified oligonucleotides, Such molecules may be attached to either end of the oligonucleotide or they may be attached at one or more internal positions. Alternatively, they may be attached to the oligonucleotide via spacers attached to the 5'- or 3'-end. Representative groups of such molecules are DNA intercalators, photochemically active groups, thermochemically active groups, chelating groups, reporter groups, and ligands. Generally all methods for labelling unmodified DNA and RNA oligonucleotides with these molecules can also be used to label L-ribo-LNA modified oligonucleotides. Likewise, all methods used for detecting labelled oligonucleotides generally apply to the corresponding labelled, L-ribo-LNA modified oligonucleotides.

Thus the use of an L-ribo-LNA modified oligonucleotide can be used for the labelling of cells, wherein the label allows the cells to be distinguishable or seperated from unlabelled cells.

Therapy

The term "strand displacement" relates to a process whereby an oligonucleotide binds to its complementary target sequence in a double stranded DNA or RNA so as to displace the other strand from said target strand.

In an aspect of the present invention, L-ribo-LNA modified oligonucleotides capable of performing "strand displacement" are exploited in the development of novel pharmaceutical drugs based on the "antigene" approach. In contrast to oligonucleotides capable of making triple helices, such "strand displacement" oligonucleotides allow any sequence in a dsDNA to be targeted and at physiological ionic strength and pH.

The "strand displacing" oligonucleotides can also be used advantageously in the antisense approach in cases where the RNA target sequence is inaccessible due to intramolecular hydrogen bonds. Such intramolecular structures may occur in mRNAs and can cause significant problems when attempting to "shut down" the translation of the mRNA by the antisense approach.

Other classes of cellular RNAs, like for instance tRNAs, rRNAs, snRNAs and scRNAs, comprise intramolecular structures that are important for their function. These classes of highly structured RNAs do not encode proteins but rather (in the form of RNA/protein particles) participate in a range of cellular functions such as mRNA splicing, polyadenylation, translation, editing, maintenance of chromosome end integrity, etc. Due to their high degree of structure, that impairs or even prevent normal oligonuclectides from hybridising efficiently, these classes of RNAs have so far been difficult to use as antisense targets. However, with the new, surprising results of α-L-ribo-LNA presented herein, targeting these RNAs with the α-L-ribo-LNA is a possibility as described below.

It is known that a number of antibiotics interact with the bacterial ribosome and thereby inhibits translation. Some antibiotics (e.g. streptomycin, tetracycline, spectinomycin, edeine, hygromycin and the neomycins) are known to bind to specific regions in the bacterial 16 S rRNA (Moazed D and Noller H F, *Nature,* 1987, 327(6121), 389). Similary, other antibiotics (e.g. chloramphenicol, erythromycin, carbomycin and vemamycin B) interacts with specific regions in the bacterial 23 S rRNA (Moazed D and Noller H F, *Biochimie,* 1987, 69(8), 879). A similar approach seems to be feasible also in higher organisms (Spangler E A and Blackburn E H, *J. Biol. Chem.,* 1985, 260(10), 6334).

Furthermore, it is known that PNAs—PNAs (Peptide Nucleic Acids) are molecules that interact specifically with DNA in a Watson—Crick base-pairing fashion and do so with a somewhat increased thermal stability ($T_m$)—targeted to functional and accessible sites in ribosomal RNA can inhibit translation in *Escherichia coli* (Good L and Nielsen P E, *Proc Natl Acad Sci USA,* 1998, 95(5), 2073) indicating that high affinity oligonucleotides which bind to certain sites of rRNA may mimic the effect of rRNA binding antibiotics. Since LNA binds to RNA with an even higher $T_m$ than PNAs do, it is highly likely that LNAs can be designed that specifically binds to bacterial rRNA and inhibits translation in the bacteria. As an extension to this approach it may be possible to exploit the small but significant differences in the rRNA sequences between higher organisms to design LNA-oligos that inhibits the translation in one, but not in the other. One obvious application of this approach would be to develop LNAs specifically which inhibit translation in *Plasmodium* spp. (the Malaria parasites), *Schistosoma* spp. (causing Bilharzia), various filariae (causing Elephantiasis and River Blindness), hookworms (causing anaemia) and other pathogenic parasites.

The use of high affinity L-ribo-LNA monomers should facilitate the construction of antisense probes of sufficient thermostability to hybridise effectively to such target RNAs. Therefore, in a preferred embodiment, L-ribo-LNA is used to confer sufficient affinity to the oligonucleotide to allow it to hybridise to these RNA classes thereby modulating the qualitative and/or quantitative function of the particles in which the RNAs are found.

The L-ribo-LNA modified oligonucleotides to be used in antisense therapeutics are designed with the dual purpose of high affinity and ability to recruit RNAseH. This can be achieved by, for instance, having L-ribo-LNA segments flanking an unmodified central DNA segment. Furthermore, the special ability of the α-L-ribo-LNA to discriminate between RNA and DNA can be exploited in various general therapeutic antisense applications because of the α-L-ribo-LNA's preference for RNA. By designing α-L-ribo-LNA oligonucleotides specific to the RNA of interest unspecific binding to DNA fragments with similar nucleotide sequence as the target RNA is avoided, thereby preventing stable association of the α-L-ribo-LNA oligonucleotides to the chromosomal DNA which can change the structure of the DNA and thus induce mutations in the gene in question. This change in DNA structure and the associated mutations may cause unwanted toxic side-effects.

Yet another embodiment of the present invention is to design ribozymes with increased specificity. Ribozymes are oligodeoxyribonucleotides and analogues thereof which combine the RNAse catalytic activity with the ability of sequence specific interaction with a complementary RNA target. These have attracted much interest as therapeutic molecules and it appears highly likely that the attractive features of α-L-ribo-LNA oligonucleotides can be used to improve the design of ribozymes directed against specific RNAs.

Yet another embodiment of the present invention is L-ribo-LNA oligonucleotides which specifically interact with cellular nucleoproteins which contain RNA as an integrated and essential component of the active protein, two examples hereof are ribosomes and telomerase. The ability of α-L-ribo-LNA oligonucleotides to inhibit telomerase can be applied to important applications.

The chromosomes of higher eukaryotes (including man) are linear. The primary structure (the DNA sequence) of the chromosome ends has been elucidated and it turns out that the DNA sequences of all chromosome ends—in a particular organism—consist of a simple repeating unit with a protruding single-stranded end. The chromosome end is called the telomere. In man telomeres contain long stretches of double stranded multiple repeats of the sequence 5'-TTAGGG-3' (sequence of one strand, in the direction from the centromere towards the chromosome end). Since all DNA polymerases require both template strand and oligonucleotide primer to initiate the synthesis of a complementary DNA strand, DNA polymerase in it self is not able to replicate the extreme ends of the chromosomes. This would lead to a progressive shortening of the chromosomes, when the chromosomes are replicated. Looking on the length of the telomeres in normal somatic cells the telomer-length indeed seems to become shorter during each cycle of replication until the telomere is only 5–15 kb in length. When the telomeres are that short, cells normally cease to divide and gradually enters the phase of senescence. The only exception to this is the stem-cells. Stem-cells are specialized cells that are able to continue to divide during the life of an organism. Interestingly the telomeres of stem-cells continues to be long (10–15 kb). They do so because of the activity of a particular enzyme, the telomerase. Telomerase is a unique enzyme that is able specifically to prolong the protruding single-stranded end of the telomere, thus allowing the telomere to be stably long. Telomerase is a ribonucleoprotein enzyme, i.e. a protein that contains an RNA and is dependant on the RNA for its enzymatic activity. The structure of telomerase is somewhat similar to reverse transcriptase—a viral protein that also is able to synthesize DNA using an RNA as template.

The enzymatic capacity of telomerase is dependant on the correct positioning of the free telomere 3' end on the RNA molecule to prolong the telomere. Molecules that are able specifically to interact with either the extreme end of the telomere or perhaps with the RNA component of telomerase will inhibit the enzyme. α-L-ribo-LNA can be designed to fulfil these requirements. This will be interesting in e.g. cancer therapy as—except for stem cells—normal somatic cells do not contain detectable telomerase activity which is in vast contrast to cancer cells, most of which contain easily detectable telomerase activity. Cancer cells are immortal, i.e. they do not senesce but continues to proliferate and form tumour mass until the organism die. The overall evidence to date suggests that the telomerase activity is essential for the immortalization of cancer cells. Interestingly, the telomeres of cancer cells are substantially shorter than the telomeres of stem cells indicating that cancer cells would hit the "telomere length barrier" earlier than stem cells would and suggesting that a drug that specifically inhibits telomerase activity is useful as an anti-cancer drug.

In this view it will be an important issue to exploit the exceptional properties of α-L-ribo-LNA to design short α-L-ribo-LNA-oligomers directed against specific parts of the telomerase RNA component with the purpose to inhibit the telomerase activity of human cancer cells.

Another embodiment of the present invention is the use of L-ribo-LNA oligonucleotides especially α-L-ribo-LNA oligonucleotides as aptamers. This promising new class of therapeutic oligonucleotides are selected in vitro to specifically bind to a given target with high affinity, such as for example ligand receptors. Their binding characteristics are likely a reflection of the ability of oligonucleotides to form three dimensional structures held together by intramolecular nucleobase pairing. It is highly likely that aptamers containing α-L-ribo-LNA oligonucleotides may display advantageous characteristics that can be exploited for therapeutic purposes.

In some cases it may be advantageous to down-regulate the expression of a gene whereas in other cases it may be advantageous to activate it. As shown by Møllegaard et al. (Møllegaard, N. E.; Buchardt, O.; Egholm, M., Nielsen, P. E. *Proc. Natl. Acad. Sci. U.S.A.* 1994, 91, 3892), oligomers capable of "strand displacement" can function as RNA transcriptional activators. In an aspect of the present invention, the LNAs capable of "strand displacement" are used to activate genes of therapeutic interest.

In chemotherapy of numerous viral infections and cancers, various forms of nucleosides and nucleoside analogues have proven effective. L-ribo-LNA nucleosides are potentially useful as such nucleoside based drugs.

In a number of cases, double-stranded RNA (DS-RNA) has been reported to have specific pharmaceutical activities. Duplexes involving fully L-ribo-LNA modified oligonucleotide(s) are potentially useful as such double-stranded drugs and it is furthermore highly possible that double-stranded α-L-ribo-LNA oligonucleotides will add important molecules to the repertoire of biologically active double-stranded RNA-like molecules.

The therapeutic potential of double-stranded LNA (DS-LNA) may therefore be in the treatment of cancer or viral infections, as explained below.

Various types of DS-RNAs either alone or in synergy with inteferon-gamma have been reported to inhibit the growth of several types of cancer cells (Borecky et al. *Tex Rep Biol Med*, 1981, 41, 575; Sharp et al. *Eur J Biochem*, 1995, 230(1), 97). DS-RNAs inhibit the growth of cancer cells in culture as well as in tumours in experimental animals. At least two double-stranded RNA-activatable enzymes seem to be involved in the tumour-suppressing activity of DS-RNA, the double-stranded RNA-activable protein kinase (PKR) and ribonuclease L (Lengyel-P, *Proc. Natl. Acad Sci USA*, 1993, 90(13), 5893). Whereas PKR is activated directly by DS-RNA, RNase L is activated by DS-RNA via (2'-5')oligoadenylate synthetase which is latent unless activated by DS-RNA. DS-RNA also induces natural killer (NK) cell activity and this activity probably contribute to the anti-tumour activity of DS-RNA.

Although naturally occurring DS-RNA typically is associated with virus infection, DS-RNA has been demonstrated to also posses anti-viral activity. DS-RNA has demonstrated its antiviral activity against the human immunodeficiency virus HIV-1 and HIV-2 (Haines et al. *J Cell Biochem*, 1991, 46(1), 9). DS-RNA and thus DS-LNA may therefore be a potential candidate as a therapeutic drug in treating AIDS.

DS-RNA has yet to prove its clinical efficacy in practice. However, mammalian cells contain a number of DS-RNA specific nucleases and perhaps because these activities DS-RNA is rapidly eliminated from patients. LNA is rather similar to RNA and shares most of the chemical characteristics of RNA (Koshkin et al., *Tetrahedron*, 1998, 54, 3607), LNA form stable duplexes and the structural change from RNA to LNA is rather subtle. Thus, it is likely that adequate double-stranded LNAs may mimic the effect of certain DS-RNAs and accordingly activate PKR and/or (2'-5')oligoadenylate synthetase and since LNA has proven itself to display exonucleolytic stability (Singh et al., *Chem. Commun.*, 1998, 455) it is possible that DS-LNA-molecules may exhibit improved therapeutic efficacy relative to DS-RNA.

The invention also concerns a pharmaceutical composition comprising a pharmaceutically active L-ribo-LNA modified oligonucleotide or a pharmaceutically active L-ribo-LNA monomer as defined above in combination with a pharmaceutically acceptable carrier.

Such compositions may be in a form adapted to oral, parenteral (intravenous, intraperitoneal), intramuscular, rectal, intranasal, dermal, vaginal, buccal, ocularly, or pulmonary administration, preferably in a form adapted to oral administration, and such compositions may be prepared in a manner well-known to the person skilled in the art, e.g. as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker.

Diagnostics

Several diagnostic and molecular biology procedures have been developed that utilise panels of different oligonucleotides to simultaneously analyse a target nucleic acid for the presence of a plethora of possible mutations. Typically, the oligonucleotide panels are immobilised in a predetermined pattern on a solid support such that the presence of a particular mutation in the target nucleic acid can be revealed by the position on the solid support where it hybridises. One important prerequisite for the successful use of panels of different oligonucleotides in the analysis of nucleic acids is that they are all specific for their particular target sequence under the single applied hybridisation condition. Since the affinity and specificity of standard oligonuclectides for their complementary target sequences depend heavily on their sequence and size this criteria has been difficult to fulfil so far.

Furthermore, a number of techniques have been developed to characterize the various types of RNA that cells may contain. A common approach to the characterization is nucleic acid hybridisation, examples of such techniques are: in situ hybridisation, dot blot hybridisation, reverse dot blot hybridisation, northern hybridisation, and reverse transcription polymerase chain reaction (rtPCR). Often these techniques are prepared on samples containing both DNA and RNA, and frequently this fact creates problems in the assays that easily could be avoided if probes existed that were adequately discriminatory between DNA and RNA. This is in particular a problem in in situ hybridisations performed on various tissue specimens. With its highly discriminative hybridization properties towards RNA an α-L-ribo-LNA oligo can be designed to specifically hybridize with the RNA in the sample thereby eliminating the possibility of erroneous results obtained from hybridization to irrelevant DNAs with the same nucleotide sequence.

In a preferred embodiment, therefore, L-ribo-LNAs can be used as a means to increase affinity and/or specificity of the probes and as a means to equalise the affinity of different oligonucleotides for their complementary sequences. As disclosed herein such affinity modulation can be accomplished by, e.g., replacing selected nucleosides in the oligonucleotide with a L-ribo-LNA carrying a similar nucleobase. In particular, this applies to α-L-ribo-LNA oligonucleotides.

In another preferred embodiment the high affinity and specificity of L-ribo-LNA modified oligonucleotides is exploited in the sequence specific capture and purification of natural or synthetic nucleic acids. In one aspect, the natural or synthetic nucleic acids are contacted with the L-ribo-LNA modified oligonucleotide immobilised on a solid surface. In this case hybridisation and capture occurs simultaneously. The captured nucleic acids may be, for instance, detected, characterised, quantified or amplified directly on the surface by a variety of methods well known in the art or it may be released from the surface, before such characterisation or amplification occurs, by subjecting the immobilised, modified oligonucleotide and captured nucleic acid to dehybridising conditions, such as for example heat or by using buffers of low ionic strength.

The solid support may be chosen from a wide range of polymer materials such as for instance CPG (controlled pore glass), polypropylene, polystyrene, polycarbonate or polyethylene and it may take a variety of forms such as for instance a tube, a micro-titer plate, a stick, a bead, a filter, etc. The L-ribo-LNA modified oligennucleotide may be immobilised to the solid support via its 5' or 3' end (or via the terminus of linkers attached to the 5' or 3' end) by a variety of chemical or photochemical methods usually employed in the immobilisation of oligonucleotides or by non-covalent coupling such as for instance via binding of a biotinylated L-ribo-LNA modified oligonucleotide to immobilised streptavidin. One preferred method for immobilising L-ribo-LNA modified oligonucleotides on different solid supports is photochemical using a photochemically active anthraquinone covalently attached to the 5'- or 3'-end of the modified oligonucleotide (optionally via linkers) as described in (WO 96/31557). Thus, the present invention also provide a surface carrying an LNA modified oligonucleotide.

In another aspect the L-ribo-LNA modified oligonucieotide cames a ligand covalently attached to either the 5'- or 3'-end. In this case the L-ribo-LMA modified oligonucleotide is contacted with the natural or synthetic nucleic acids in solution whereafter the hybrids formed are captured onto a solid support carrying molecules that can specifically bind the ligand.

In still another aspect, L-ribo-LNA modified oligonucleotides capable of performing "strand displacement" are used in the capture of natural and synthetic nucleic acids without prior denaturation. Such modified oligonucleotides are particularly useful in cases where the target sequence is difficult or impossible to access by normal oligonucleotides due to the rapid formation of stable intramolecular structures. Examples of nucleic acids comprising such structures are rRNA, tRNA, snRNA and scRNA.

In another preferred embodiment, L-ribo-LNA modified oligonucleotides designed with the purpose of high specificity are used as primers in the sequencing of nucleic acids and as primers in any of the several well known amplification reactions, such as the PCR reaction. As shown herein, the design of the L-ribo-LNA modified oligonucleotides determines whether it will sustain an exponential or linear target amplification. The products of the amplification reaction can be analysed by a variety of methods applicable to the analysis of amplification products generated with normal DNA primers. In the particular case where the L-ribo-LNA modified oligonucleotide primers are designed to sustain a linear amplification the resulting amplicons will carry single stranded ends that can be targeted by complementary probes without denaturation. Such ends could for instance be used to capture amplicons by other complementary L-ribo-LNA modified oligonucleotides attached to a solid surface.

In another aspect, L-ribo-LNA modified oligos capable of "strand displacement" are used as primers in either linear or exponential amplification reactions. The use of such oligos is expected to enhance overall amplicon yields by effectively competing with amplicon rehybridisaton in the later stages of the amplification reaction. Demers et al. (*Nucl. Acid Res.* 1995, 23, 3050–3055) discloses the use of high-affinity, non-extendibie oligos as a means of increasing the overall yield of a PCR reaction. It is believed that the oligomers elicit these effects by interfering with amplicon re-hybridisation in the later stages of the PCR reaction. It is expected that L-ribo-LNA modified oligos blocked at their 3' end will provide the same advantage. Blocking of the 3' end can be achieved in numerous ways like for instance by exchanging the 3' hydroxyl group with hydrogen or phosphate. Such 3' blocked L-ribo-LNA modified oligos can also be used to selectively amplify closely related nucleic acid sequences in a way similar to that described by Yu et al. (*Biotechniques,* 1997, 23, 714–716).

In recent years, novel classes of probes that can be used in for example real-time detection of amplicons generated by target amplification reactions have been invented. One such class of probes have been termed "Molecular Beacons". These probes are synthesised as partly self-complementary oligonucleotides comprising a fluorophor at one end and a quencher molecule at the other end. When free in solution the probe folds up into a hairpin structure (guided by the self-complimentary regions) which positions the quencher in sufficient closeness to the fluorophor to quench its fluorescent signal. Upon hybridisation to its target nucleic acid, the hairpin opens thereby separating the fluorophor and quencher and giving off a fluorescent signal.

Another class of probes has been termed "Taqman probes". These probes also comprise a fluorophor and a quencher molecule. Contrary to the Molecular Beacons, however, the quenchers ability to quench the fluorescent signal from the fluorophor is maintained after hybridisation of the probe to its target sequence. Instead, the fluorescent signal is generated after hybridisation by physical detachment of either the quencher or fluorophor from the probe by the action of the 5'exonuxlease activity of a polymerase which has initiated synthesis from a primer located 5' to the binding site of the Taqman probe.

High affinity for the target site is an important feature in both types of probes and consequently such probes tends to be fairly large (typically 30 to 40 mers). As a result, significant problems are encountered in the production of high quality probes. In a preferred embodiment, therefore, LNA is used to improve production and subsequent performance of Taqman probes and Molecular Beacons by reducing their size whilst retaining the required affinity.

In a further aspect, L-ribo-LNAs are used to construct new affinity pairs (either fully or partially modified oligonucleotides). The affinity constants can easily be adjusted over a wide range and a vast number of affinity pairs can be designed and synthesised. One part of the affinity pair can be attached to the molecule of interest (e.g. proteins, amplicons, enzymes, polysaccharides, antibodies, haptens, peptides, PNA, etc.) by standard methods, while the other part of the affinity pair can be attached to e.g. a solid support such as beads, membranes, microliter plates, sticks, tubes, etc. The solid support may be chosen from a wide range of polymer materials such as for instance polypropylene, polystyrene, polycarbonate or polyethylene. The affinity pairs may be used in selective isolation, purification, capture and detection of a diversity of the target molecules mentioned above.

The principle of capturing a L-ribo-LNA-tagged molecule by ways of interaction with another complementary L-ribo-LNA oligonuclectide (either fully or partially modified) can be used to create an infinite number of novel affinity pairs.

In another preferred embodiment the high affinity and specificity of L-ribo-LNA modified oligonucleotides are exploited in the construction of probes useful in in-situ hybridisation. For instance, L-ribo-LNA could be used to reduce the size of traditional DNA probes while maintaining the required affinity thereby increasing the kinetics of the probe and its ability to penetrate the sample specimen.

Purification

Another embodiment of the present invention is to use the L-ribo-LNA oligonucleotides especially α-L-ribo-LNA oiigonucleotides in RNA-specific purification procedures. The methods traditionally employed to isolate nucleic acids from prokaryotic cells, eukaryotic cells or from complex biological samples uses organic solvents such as phenol and chloroform. These nucleic acid isolations typically begin with an enzymatic digest of the sample performed with proteases followed by cell lysis using ionic detergents and then extraction with phenol or a phenol/chloroform combination. The organic and aqueous phases are separated and nucleic acids which have partitioned into the aqueous phase are recovered by precipitation with alcohol. However, phenol or a phenol/chloroform mixture is corrosive to human skin and is considered as hazardous waste which must be carefully handled and properly discarded. Additionally, standard extractions using the phenol/chloroform methods result in mixtures of RNA and DNA. Therefore it is advantageous to prepare nucleic acid isolation by exploiting the ability of α-L-ribo-LNA to discriminate between RNA and DNA, thereby obtaining samples of pure RNA.

Kits

The present invention also provides a kit for the isolation, purification, amplification, detection, identification, quantification, or capture of natural or synthetic nucleic acids, where the kit comprises a reaction body and one or more L-ribo-LNA modified oligonucleotides (oligomer) as defined herein. The L-ribo-LNA modified oligonucleotides are preferably immobilised onto said reaction body.

The present invention also provides a kit for the isolation, purification, amplification, detection, identification, quantification, or capture of natural or synthetic nucleic acids, where the kit comprises a reaction body and one or more L-ribo-LNAs as defined herein. The L-ribo-LNAs are preferably immobilised onto said reactions body (e.g. by using the immobilising techniques described above).

For the kits according to the invention, the reaction body is preferably a solid support material, e.g. selected from borosilicate glass, soda-lime glass, polystyrene, polycarbonate, polypropylene, polyethylene, polyethyleneglycol terephthalate, polyvinylacetate, polyvinyl-pyrrolidinone, polymethylmethacrylate and polyvinylchloride, preferably polystyrene and polycarbonate. The reaction body may be in the form of a specimen tube, a vial, a slide, a sheet, a film, a bead, a pellet, a disc, a plate, a ring, a rod, a net, a filter, a tray, a micro-titre plate, a stick, or a multi-bladed stick.

The kits are typically accompanied by a written instruction sheet stating the optimal conditions for use of the kit.

EXPERIMENTAL

General

Reactions were conducted under an atmosphere of nitrogen when anhydrous solvents were used. Column chromatography was carried out on glass columns using Silica gel 60 (0.040–0.063 mm). After column chromatography, fractions containing product were pooled, evaporated to dryness under reduced pressure and dried under vacuum to give the product. After drying organic phases using $Na_2SO_4$, filtration was performed. Petroleum ether of distillation range 60–80° C. was used. Chemical shift values δ are in ppm relative to tetramethylsilane as internal reference ($^1$H and $^{13}$C NMR) and relative to 85% $H_3PO_4$ ($^{31}$P NMR). Microanalyses were performed at The Microanalytical Laboratory, Department of Chemistry, University of Copenhagen.

The specific descriptions below are accompanied by FIGS. 1–4 and Tables 1–3.

Preparation of L-ribo-LNA Monomers

Example 1

5-O-Benzoyl-4-C-benzoyloxymethyl-3-O-benzyl-1, 2-O-isopropylidene-α-D-glucofuranose (2)

To a stirred ice cold solution of 3—O-benzyl-4-C-hydroxymethyl-1,2-isopropylidene-α-D-glucofuranose (1) (5.00 g, 0.016 mol) in anhydrous pyridine (60 cm³) was added benzoyl chloride (4.1 cm³, 0.035 mol). After stirring at room temperature for 4 h, the reaction mixture was cooled to 0° C., $H_2O$ (50 cm³) was added, and the mixture was extracted with dichloromethane (100 cm³×3). The combined organic phase was washed with saturated aqueous solutions of sodium hydrogen carbonate (30 cm³×3) and brine (20 cm³×3), dried ($Na_2SO_4$) and evaporated to dryness under reduced pressure. The residue was purified by silica gel column chromatography using first petroleum ether/dichloromethane (1:1, v/v) and then dichloromethanelmethanol (99:1, v/v) as eluent to give furanose 2 (7.50 g, 90%) as a yellowish oil after evaporation of the solvents under reduced pressure. $δ_H$ ($CDCl_3$) 8.02–7.23 (15H, m), 6.08 (1H, d, J 4.2), 4.81–4.50 (7H, m), 4.22 (1H, d, J 1.0), 1.59 (3H, s), 1.37 (3H, s). $δ_C$ ($CDCl_3$) 166.1, 165.8, 136.7, 133.1, 133.0, 129.9, 129.7, 129.6, 129.5, 128.5, 128.4, 128.3, 128.0, 127.9, 113.3, 105.4, 86.4, 85.1, 83.8, 72.3, 64.3, 63.8, 27.0, 26.4. FAB-MS m/z 521 $[M+H]^{30}$. Found (%) C, 69.1; H, 5.9, $C_{30}H_{32}O8$ requires C, 69.2; H, 6.2.

Example 2

5-O-Benzoyl-4-C-benzoyloxymethyl-3-O-benzyl-1, 2-di-O-acetyl-D-glucofuranose (3)

A solution of furanose 2 (7.40 g, 0.014 mol) in 80% acetic acid (60 cm³) was stirred 9 h at 90° C. The mixture was evaporated to dryness under reduced pressure and the residue was coevaporated with toluene (10 cm³×3) and dissolved in anhydrous pyridine (80 cm³). Acetic anhydride (5.5 cm³) was added and the solution was stirred for 46 h at room temperature. The mixture was evaporated to dryness under reduced pressure and the residue was coevaporated with toluene (10 cm³×3) and dissolved in dichloromethane (150 cm³). The solution was washed with saturated aqueous solutions of sodium hydrogen carbonate (30 cm³×3) and brine (30 cm³×3), dried ($Na_2SO_4$) and concentrated under reduced pressure. The residue was purified by silica gel column chromatography using first petroleum ether/dichloromethane (1:1, v/v) and then dichloromethane/methanol (99:1, v/v) as eluent to give the anomeric mixture 3 (α:β=3: 1, 7.33 g, 92%) as a clear oil after evaporation of the solvents under reduced pressure. This oil was used in the next step without further purification. $δ_C$ ($CDCl_3$) 169.4, 169.0, 165.8, 165.6, 137.0, 133.2, 133.1, 133.0, 129.6, 129.5, 129.2, 128.3, 127.8, 127.7, 127.4, 99.4, 92.3, 87.0, 83.2, 82.2, 80.7, 77.4, 76.9, 76.3, 73.2, 72.4, 20.9, 20.8, 20.6, 20.3. FAB-MS m/z 562 $[M]^+$.

Example 3

1-(2-O-Acetyl-5-O-benzoyl-4-C-benzoyloxymethyl-3-O-benzyl-β-D-xylofuranosyl)thymine (4)

To a stirred suspension of the anomeric mixture 3 (7.26 g, 0.013 mol) and thymine (3.25 g, 0.028 mol) in anhydrous acetonitrile (80 cm³) was added N,O-bis(trimethylsilyl)acetamide (19.1 cm³, 0.077 mol). The reaction mixture was stirred at 60° C. for 1 h and then cooled to 0° C. Trimethylsilyl triflate (4.1 cm³, 0.023 mol) was added drop-wise during 10 min and the mixture was subsequently heated for 22 h under reflux. After cooling to room temperature, a saturated aqueous solution of sodium hydrogen carbonate (30 cm³) was added and extraction was performed using dichloromethane (100 cm³×3). The combined organic phase was washed with saturated aqueous solutions of sodium hydrogen carbonate (30 cm³×3) and brine (50 cm³×3), dried ($Na_2SO_4$) and concentrated under reduced pressure. The residue was purified by silica gel column chromatography using dichloromethane/methanol (0.5–2.0% methanol, v/v) as eluent to give nucleoside 4 (6.88 g, 85%) as a white solid material after evaporation of the solvents under reduced pressure. $\delta_H$ (CDCl$_3$) 8.97 (1H, br s), 8.04–7.23 (16H, m), 6.37 (1H, d, J 3.6), 5.42 (1H, t, J 3.1), 4.89–4.56 (6H, m), 4.22 (1H, d, J 2.6), 2.13 (3H, s), 1.74 (1H, d, J 0.8) $\delta_C$ (CDCl$_3$) 169.9, 166.0, 165.7, 163.4, 150.4, 136.2, 135.2, 133.5, 133.4, 129.8, 129.7, 129.6, 129.5, 129.0, 128.6, 128.4, 128.2, 112.0, 87.4, 86.0, 81.3, 80.3, 72.6, 63.1, 82.9, 20.8, 12.3. FAB-MS m/z 629 [M+H]$^+$. Found (%) C, 64.4; H, 4.9; N, 4.4; C$_{34}$H$_{32}$N$_2$O$_{10}$,0.25H$_2$O requires C, 64.5; H, 5.1; N, 4.4.

Example 4

1-(3-O-Benzy-4-hydroxymethyl-β-D-xylofuranosyl) thymine (5)

To a stirred solution of nucleoside 4 (9.00 g, 0.014 mol) in methanol (130 cm$^3$) was added sodium methoxide (3.87 g, 0.0716 mol). The reaction mixture was stirred at room temperature for 4 h and then neutralized with dilute hydrochloric acid. The mixture was evaporated to dryness under reduced pressure followed by coevaporation using toulene (15 cm$^3$×3) The residue was purified by silica gel column chromatography using dichloromethane/methanol (4–15% methanol, v/v) as eluent to give nucleoside triol 5 (4.82 g, 89%) as a white solid material after evaporation of the solvents under reduced pressure. $\delta_H$ (CD$_3$OD) 7.89 (1H, d, J 1.2), 7.40–7.24 (5H, m), 5.97 (1H, d, J 6.2), 4.83–4.65 (2H, m), 4.53 (1H, t, J 6.2), 4.21 (1H, d, J 6.2), 3.84 (1H, d, J 12.0), 3.63 (1H, d, J 12.0), 3.59 (2H, d. J 2.6), 1.82 (1H, d, J 1.1). $\delta_C$ (CD$_3$OD) 164.4, 150.9, 137.5, 136.6, 127.5, 127.0, 126.9, 109.8, 86.7, 86.4, 82.8, 78.0, 72.1, 62.3, 61.1, 10.5 (CH$_3$). FAB-MS m/z 379 [M+H]$^+$. Found (%) C, 56.2; H, 6.0; N, 7.0; C$_{18}$H$_{22}$N$_2$O$_7$,0.25H$_2$O requires C, 56.5; H, 5.9; N, 7.3.

Example 5

1-(3-O-Benzyl-4-C-(4,4'-dimethoxytrityloxymethyl)- β-D-xylofuranosyl)thymine (6)

To a solution of nucleoside 1-(3-O-Benzyl-4-C-hydroxymethyl-β-D-xylofuranosyl)thymine 5 (5.38 g, 14.2 mmol) in anhydrous tetrahydrofuran (400 cm$^3$) was added AgNO$_3$ (2.66 g, 15.7 mmol) followed by anhydrous pyridine (5.7 cm$^3$) and 4,4'-dimethoxytrityl chloride (5.30 g, 15.6 mmol). The mixture was stirred in the dark under nitrogen for 18 h at room temperature. The reaction was quenched by addition of a saturated aqueous solution of sodium hydrogen carbonate (10 cm$^3$) and the resulting mixture was extracted with dichloromethane. The combined organic phase was evaporated to dryness under reduced pressure and the residue was co-evaporated with toluene and was purified by silica gel column chromatography using dichloromethane/ methanol/pyridine (0.5% methanol; 0.5% pyridine, v/v) as eluent to afford nucleoside 6 (3.13 g, 31%) as a white foam after evaporation of the solvents. $\delta_C$ ((CD$_3$)$_2$SO) 164.1 (C-4), 158.4, 145.1, 138.5, 137.0, 135.9, 135.7, 130.1, 130.1, 129.2, 128.5, 128.5, 128.2, 128.1, 127.7, 127.6, 127.0, 125.7, 113.5 (DMT, benzyl, C-6), 151.4 (C-2), 110.1 (C-5), 85.8, 85.2, 84.6, 83.5 (C-1', C-3', C-4', DMT), 76.8 (C-2'), 72.3 (CH$_2$Ph), 65.2 (C-5"), 62.1 (C-5'), 55.4 (2× CH$_3$O), 12.6 (5-CH$_3$).

Example 6

1-(3-O-Benzyl-4-C-(4,4'-dimethoxytrityloxymethyl)- 2,5-di-O-(p-toluenesulphonyl)-β-D-xylofuranosyl) thymine (7)

To a solution of nucleoside 6 (2.79 g, 3.9 mmol) in anhydrous pyridine (50 cm$^3$) was added a catalytic amount of 4-(N,N-dimethylamino)pyridine and p-toluenesulphonyl chloride (6.50 g, 34 mmol). The mixture was stirred in the dark for 24 h at room temperature under nitrogen. The reaction was quenched by addition of a saturated aqueous solution of sodium hydrogen carbonate (100 cm$^3$) and the resulting mixture was extracted with dichloromethane. The combined organic phase was washed with saturated aqueous solutions of sodium hydrogen carbonate (3×75 cm$^3$) and sodium chloride (2×75 cm$^3$). The separated organic phase was dried (Na$_2$SO$_4$) and evaporated to dryness under reduced pressure. The residue was purified by silica gel column chromatography using dichloromethane/methanol/ pyridine (0.5% methanol; 0.5% pyridine, v/v) as eluent to afford nucteoside 7 (2.40 g, 62%) as a yellowish foam after evaporation of the solvents. $\delta_C$ ((CD$_3$)$_2$SO) 163.2 (C-4), 158.2, 145.9, 145.1, 144.3, 136.8, 135.0, 134.9, 134.8, 131.8, 131.6, 130.2, 130.0, 129.7, 128.2, 127.9, 127.8, 127.6, 127.5, 127.5, 127.4, 126.8, 113.3 (DMT, C-6, 2×Ts, benzyl), 150.2 (C-2), 110.8 (C-5), 95.0, 86.2 (DMT, C-4'), 82.2, 81.9 (C-1', C-2'), 81.2 (C-3'), 72.9 (CH$_2$Ph), 79 (C-5"), 64 (C-5'), 55.1 (2×CH$_3$O), 21.2, 21.2 (2×CH$_3$), 12.0 (5-CH$_3$).

Example 7

(1R,3R,4S,7R)-7-Benzyloxy-1-(4,4'-dimethoxytrityloxymethyl)-3-(thymin-1-yl)-2,5-dioxabicyclo[2.2.1] heptane (8)

To a solution of nucleoside 7 (3.87 g, 3.92 mmol) in a mixture of ethanol and H$_2$O (1:1, v/v) was added an aqueous solution of NaOH (2M, 8 cm$^3$). The mixture was heated under reflux for 24 h and after cooling extracted with dichloromethane. The combined organic phase was washed with a saturated aqueous solution of sodium hydrogen carbonate (2×75 cm$^3$) and evaporated to dryness under reduced pressure. The residue was purified by silica gel column chromatography using dichloromethane/methanol/ pyridine (0.5% methanol; 0.5% pyridine, v/v) as eluent to afford nucleoside 8 (2.10 g, 81%) as a white foam after evaporation of the solvents $\delta_C$ ((CD$_3$)$_2$SO) 163.8 (C-4), 158.2, 158.1, 144.7, 137.7, 135.9, 135.2, 135.1, 129.8, 129.7, 128.3, 127.9, 127.7, 127.7, 127.4, 126.7, 113.35 (DMT, benzyl, C-6) 150.3 (C-2), 108.1 (C-5), 88.4, 85.5 (C-4', DMT), 86.4 (C-1'), 79.5 (C-2'), 76.3 (C-3'), 72.6 (C-5'), 71.2 (CH$_2$Ph), 58.9 (C-5"), 55.1 (2×CH$_3$O), 12.4 (5-CH$_3$).

Example 8

(1R,3R,4S,7R)-1-(4,4'-Dimethoxytrityloxymethyl)- 7-hydroxy-3-(thymin-1-yl)-2,5-dioxabicyclo[2.2.1] heptane (9)

To a solution of nucleoside 8 (1.09 g, 1.65 mmol) in methanol (30 cm$^3$) was added ammonium formate (0.33 g, 5.29 mmol). A catalytic amount of Pd/C suspended in methanol (10 cm$^3$) was added and the mixture was heated for 2 h under reflux. After cooling to room temperature, the mixture was evaporated to dryness under reduced pressure and the residue was purified by silica gel column chromatography using dichloromethane/methanol/pyridine (2% methanol; 0.5% pyridine, v/v) as eluent to afford nucleoside 9 (0.76 g, 80%) as a white solid material after evaporation of the solvents. $\delta_C$ ((CD$_3$)$_2$SO) 163.9 (C-4), 158.2, 144.8, 135.8, 135.4, 135.3, 129.8, 127.9, 127.7, 126.8. 113.3 (DMT, C-6), 150.4 (C-2), 108.0 (C-5), 89.2, 85.4 (C-4', DMT), 86.4 (C-1'), 78.9 (C-2'), 72.9 (C-3'), 72.3 (C-5'), 59.9 (C-5"), 55.1 (2×CH$_3$O), 12.5 (5-CH$_3$).

Example 9

(1R,3R,4S,7R)-7-(2-Cyanoethoxy(diisopropylamino)phosphinoxy)-1-(4,4'-dimethoxytrityloxymethyl)-3-(thymin-1-yl)-2,5-dioxabicyclo[2.2.1]heptane(10)

To a solution of nucleoside 9 (420 mg, 0.73 mmol) in anhydrous dichloromethane (4 cm$^3$) was added N,N-diisopropylethylamine (0.4 cm$^3$) and 2-cyanoethyl N,N-diisopropyl-phosphoramidochloridite (0.4 cm$^3$). The mixture was stirred in the dark under nitrogen for 18 h at room temperature. The reaction was quenched by addition of methanol and the mixture was diluted with ethyl acetate (10 cm$^3$), washed with saturated aqueous solutions of sodium hydrogen carbonate (3×10 cm$^3$) and sodium chloride (2×10 cm$^3$) and was evaporated to dryness under reduced pressure. The residue was co-evaporated with anhydrous acetonitrile and was purified by silica gel column chromatography using petroleum ether/ethyl acetate/pyridine (30–40% ethyl acetate; 0.2% pyridine, v/v) as eluent to give an oli. This oil was dissolved in dichloromethane (1 cm$^3$) and a product was precipitated from petroleum ether (20 cm$^3$) at −40° C. with vigorous stirring. The precipitate was collected by filtration and co-evaporated with anhydrous acetonitrile to give nucleoside 10 (117 mg, 21%) as a white foam. $\delta_P$ (CH$_3$CN) 149.9, 149.3.

Preparation of LNA Oligonucleotides

Example 10

Synthesis of Unmodified Oligonucleotides and Oligonucleotides Comprising L-ribo-LNA Derived from Phosphoramidite 10 (formula X)

L-ribo-LNA and reference oligonucleotides were prepared on a Biosearch 8750 DNA Synthesizer. Coupling of amidite 10 was performed by "hand coupling" (premixing amidite and the activator in acetonitrile in a syringe; then flushing the column reactor approximately twice every minute throughout the coupling time applied; CPG solid supports). Synthesis of the L-ribo-LNAs were accomplished using pyridine hydrochloride as activator (10–30 min coupling time; stepwise coupling yields for amidite 10 were 96–99%). The unmodified 2'-deoxynucleoside 2-cyanoethyl N,N-diisopropylphosphoramidites were coupled by use of the standard DNA-program of the synthesiser except for the couplings immediately following an X monomer which were conducted according to the RNA program of the synthesiser. After completion of the sequences, deprotection using concentrated ammonia in methanol (32% (w/w), room temperature, 12 h) of 5'-O-DMT-ON oligos and subsequently reversed phase purification (commercially available disposable cartridges (Cruachem); procedure includes detritylation) yielded the final oligomeric products. However, for the unmodified oligonucleotldes and the L-ribo-LNA comprising only one X monomer the 5'-O-DMT group was removed on the synthesiser immediately after completion of the sequences. Subsequent treatment with concentrated ammonia in methanol (32% (w/w), 12 h, 55° C.) and ethanol precipitation afforded the product oligomers. Capillary gel electrophoresis was used to analyse the purity of the synthesised L-ribo-LNAs.

Hybridisation Data

Example 11

Thermostability of Oligonucleotides Comprising Monomer X

The thermostability of the L-ribo-LNA modified oligo-nucleotides were determined spectrophotometrically using a spectrophotometer equipped with a thermoregulated Peltier element. Hybridisation mixtures of 1 ml were prepared using a medium salt buffer solution (10 mM Na$_2$HPO$_4$, pH 7.0, 100 mM NaCl, 0.1 mM EDTA) and equimolar (1 μM or 1.5 μM) amounts of the different L-ribo-LNA modified oligonucleotides and their complementary DNA or RNA oligonucleotides. Identical hybridisation mixtures using the unmodified oligonucleotides were prepared as references. The absorbance at 260 nm was recorded while the temperature was raised linearly from 10–90° C. (1° C./min). The melting temperatures (T$_m$ values) were obtained as the maxima (+/−1° C.) of first derivative of the melting curves. Tables 1–3 summarise the results (L-ribo-LNAs are marked with bold). FIG. 2 illustrates the monomeric L-ribo-LNA used.

From Table 1 it can be seen that incorporation of one or more consecutive α-L-ribo-LNA monomers X into an oligonucleotide sequence (A) and (B), does not change the binding affinity of the α-L-ribo-LNAs toward complementary DNA, while the binding affinity towards complementary RNA is strongly increased.

Table 2 shows binding studies of homo-tyhmine diastereoisomeric LNAs towards RNA (rA$_{14}$), singly mis-matched RNA (5'-r(A$_6$CA$_7$)), enantiomeric RNA (ent-rA$_{14}$) and singly mis-matched enantiomeric RNA (ent-5'-r(A$_6$CA$_7$)).

Table 3 shows binding studies of mixed-sequence 9-mer DNA, LNA and α-L-ribo-LNA.

Alternative Method

Example 12

1-(3-O-Benzyl-2,5-di-O-methanesulfonyl-4-C-(methanesulfonyloxymethyl)-β-D-xylofuranosyl) thymine (11)

To a solution of nucleoside 5 (1100 mg, 2.91 mmol) in anhydrous tetrahydrofuran (20 cm$^3$) was added anhydrous pyridine (5 cm$^3$) followed by methanesulfonyl chloride (1.2 ml, 15.5 mmol). The mixture was stirred under a nitrogen atmosphere for 18 h at room temperature. The reaction mixture was evaporated to dryness under reduced pressure and dissolved in ethyl acetate. The organic phase was washed with saturated aqueous solution of sodium hydrogen carbonate (3×10 cm$^3$) and dried (Na$_2$SO$_4$). The organic phase was evaporated to dryness under reduced pressure. The residue was purified by silica gel column chromatography using dichloromethane/methanol (2% methanol, v/v) as elutxnt to afford nucleoside 11 (908 mg, 51%). $\delta_C$ (CDCl$_3$) 163.3, 150.6, 135.6, 134.6, 128.7, 128.3, 112.2, 87.9, 85.0, 83.1, 80.9, 77.2, 76.9, 76.6, 73.3, 66.6, 66.2, 38.6, 37.6, 37.6, 12.2.

Example 13

(1R,3R,4S,7R)-1-(Hydroxymethyl)-7-benzyloxy-3-(thymin-1-yl)-2,5-dioxabicyclo-[2.2.1]heptane (12)

To a solution of nucleoside 11 (329 mg, 0.54 mmol) in ethanol/water (10 cm$^3$, 1:1, v/v) was added 6M NaOH (aq) (0.9 ml, 5.4 mmol). The mixture was refluxed at 80° C. for 43 h followed by evaporation to dryness under reduced pressure. The residue was purified by silica gel column chromatography using dichloromethane/methanol (2.4% methanol, v/v) as eluent to afford nucleoside 12 (85 mg, 44%). δ$_C$ ((CD$_3$)$_2$SO) 163.8, 150.3, 138.0, 135.8, 128.3, 127.7, 127.5, 108.0, 90.2, 86.5, 86.4, 79.3, 76.5, 72.5, 71.2, 57.2, 40.2, 40.0, 39.8. 39.6, 39.4, 39.2, 39.0, 12.3.

Example 14

Synthesis of Nucleoside 8 from Nucleoside 12

Standard DMT-protection of the primary hydroxy group of nucleoside 12 (e.g. using the same procedure as for preparation of nucleoside 6 by DMT-protection of the primary hydroxy group of nucleoside 5) would give nucleoside 8 which can be used in the synthesis of α-L-ribo-LNA nucleoside phosphoramidite derivative 10 (see FIG. 2 and the relevant examples).

Example 15

9-(2-O-Acetyl-5-O-benzoyl-4-C-(benzoyloxymethyl)-3-O-benzyl-α-L-ribofuranosyl)-6-N-benzoyladenine (14)

Sugar 3 (2.05 g) was dissolved in anhydrous acetonitrile (30 mL). N-6-Benzoyladenine (1.86 g) followed by SnCl$_4$ (1.3 mL) were added and the resulting mixture was stirred at room temperature for 3.7 h whereupon a saturated aqueous solution of NaHCO$_3$ was added until neutralization. After filtration through Celite, the filtrate was washed successively with a saturated aqueous solution of NaHCO$_3$ (3×150 mL) and H$_2$O (2×150 mL), dried (Na$_2$SO$_4$) and evaporated to dryness under reduced pressure. The residue was purified by silica gel column chromatography (40–60% NaOAc in petroleum ether) to give a fully protected nucleoside intermediate (1.40 g, 52% yield). This intermediate (1.29 g) was dissolved in methanol (35 mL) and a saturated solution of NH$_3$ in methanol (35 mL) was added. After stirring at 0° C. for 2.3 h, the mixture was evaporated to dryness under reduced pressure and the residue was purified by by silica gel column chromatography (1% methanol in dichloromethane) to give an intermediate which was dissolved in anhydrous dichloromethane (40 mL). After cooling to −50° C., an hydrous pyridine (3 mL) was added together with trifluoromethanesulfonic anhydride (0.65 mL). After stirring for 50 min, additional trifluoromethanesulfonic anhydride (0.65 mL) was added and stirring was continued at −10° C. for 1 h. Dichloromethane (100 mL) was added and washing was performed using a saturated aqueous solution of NaHCO$_3$ (3×100 mL). The separated organic phase was dried (Na$_2$SO$_4$) and evaporated to dryness under reduced pressure to give an intermediate. This intermediate was dissolved in toluene (20 mL) and KOAc (0.85 g) and 18-crown-6 (0.92 g) were added and the resulting mixture was stirred at 80° C. for 7 h whereupon evaporation to dryness under reduced pressure afforded a residue which was purified by silica gel column chromatography (0–1.5% methanol in dichloromethane) to give nucleoside 14 (1.1 g, 84% for three steps). δ$_C$ (CDCl$_3$) 168.8, 165.8, 142.7, 136.0, 133.5, 133.3, 132.7. 129.6, 129.6, 128.8, 128.6, 128.5, 128.4, 128.4, 128.1, 127.8, 83.8, 82.2, 78.4, 74.3, 70.8, 64.7, 63.4, 20.5. MS (m/z) 742.0 [M+H]$^+$.

Example 16

(1R,3R,4S,7R)-7-Benzyloxy-1-hydroxymethyl-3-(N-6-benzoyladenin-9-yl)-2,5-dioxabicyclo[2.2.1]heptane (15)

Nucleoside 14 (3.05 g) was dissolved in a saturated solution of NH$_3$ in methanol (200 mL) and stirred at room temperature for 4 days whereupon a 33% aqueous solution of NH$_3$ (60 mL) was added and stirring was continued for 4 h. The mixture was evaporated to dryness under reduced pressure to give an intermediate which was dissolved in anhydrous pyridine (100 mL). TMSCI (7.8 mL) was added and stirring was continued at room temperature for 5 h. After cooling to 0° C., benzoyl chloride (2.4 mL) was added and stirring was continued at room temperature for 16 h. H$_2$O (50 mL) was added followed after 5 min by a 25% saturated aqueous solution of NH$_3$ (25 mL). After stirring for 20 min at room temperature, the mixture was evaporated to dryness under reduced pressure and the residue was purified by silica gel column chromatography (2–5% methanol in dichloromethane) to give an intermediate (1.76 g, 87% over two steps) This intermediate (325 mg) was dissolved in anhydrous pyridine (50 mL) and mesyl chloride (0.11 mL) was added at 0° C. under stirring. After stirring for 2 h, H$_2$O (5 mL) was added and the volume of the mixture was reduced to approximately 50% by evaporation under reduced pressure. Dichloromethane (100 mL) was added, and washing was performed with a saturated aqueous solution of NaHCO$_3$ (3×20 mL). The organic phase was dried (Na$_2$SO$_4$) and evaporated to dryness under reduced pressure. The residue was purified by silica gel column chromatography (2–4% methanol in dichloromethane) to give an intermediate (284 mg). This intermediate (354 mg) was dissolved in a mixture of dioxane (15 mL), H$_2$O (15 mL) and 2 M NaOH (5.5 mL). After stirring for 72 h under reflux, a 7% (w/w) solution of HCl in dioxane was added until neutralization. Washing was performed with a saturated aqueous solution of NaHCO$_3$ (2×100 mL) and the organic phase was dried (Na$_2$SO$_4$) and evaporated to dryness under reduced pressure. The residue was purified by silica gel column chromatography (0–4% methanol in dichloromethane) to give the bicyclic nucleoside 15 (24 mg). Δ$_C$ ((CD$_3$)$_2$SO) 156.0, 152.6, 149.4, 138.8, 138.0, 128.3, 127.7, 127.5, 118.3, 89.7, 83.9, 79.7, 77.0, 73.0, 71.2, 57.2. δ$_H$ ((CD$_3$)$_2$SO) 8.38 (1H, s), 8.14 (1H, s), 7.40–7.30 (7H, m), 6.37 (1H, s), 5.06 (1H, t, J 5.8 Hz), 4.73–4.66 (3H, m), 4.46 (1H, s), 4.15 (1H, d, J 8.4 Hz), 4.04 (1H, d, J 8.2 Hz), 3.75 (2H, d, J 5.7 Hz).

Example 17

(1S,3R,4S,7R)-7-(2-Cyanoethoxy(diisopropylamino)phosphinoxy)-1-(4,4'-dimethoxytrityloxymethyl)-3-(6-N-benzoyladenin-9-yl)-2,5-dioxabicyclo[2.2.1]heptane (16)

DMT-protection of nucleoside 15 followed by debenzylation and 3'-O-phosphitylation is expected to furnish phosphoramidite derivative 16. Another possible route affording 16 from nucleoside 15 is debenzylation of 15 followed by selective DMT-protection of the primary hydroxyl group and eventual 3'-O-phosphitylation. The reactions outlined in this example follows standard procedures (See, e.g.: Koshkin, A. A., Singh, S. K., Nielsen, P., Rajwanshi, V. K., Kumar, R., Meldgaard, M., Olsen. C. E., Wengel, J. *Tetrahedron* 1998, 54, 3607).

TABLE 1

| Sequence[a] | | $T_m$ (° C.)[b] | $T_m$ (° C.)[c] |
|---|---|---|---|
| 5'-$T_7XT_6$ | (A) | 32 | 33 |
| 5'-$T_5X_4T_5$ | (C) | 36 | 46 |
| 5'-$T_3(Y)_4(X)_4T_3$ | (F) | 64 | 63 |
| 5'-$X_9T$ | (G) | 63 | 66 |
| 5'-$T_{10}$ | (E') | 24/20 | 18 |
| 5'-$T_{14}$ | (E) | 32 | 28 |

[a]X = monomer derived from phosphoramidite 10
Y = LNA monomers containing a 2'-O,4'-C-methylene bridge, cf. Singh et al. (above)
[b]Complexed with 5'-$dA_{14}$
[c]Complexed with 5'-$rA_{14}$

TABLE 2

| Sequence[a] | $rA_{14}$ $T_m$ (° C.) | 5'-$r(A_5CA_7)$ $T_m$ (° C.) | ent-$rA_{14}$ $T_m$ (° C.) | ent-5'-$r(A_6CA_7)$ $T_m$ (° C.) |
|---|---|---|---|---|
| $T_{10}$ | 18 | no $T_m^c$ | no $T_m^c$ | no $T_m^c$ |
| 5'-$(Y)_9T$ | 71 | 61 | 52 | 51 |
| 5'-$(X)_9T$ | 66 | 49 | 39 | no $T_m^c$ |
| 5'-(xylo-$Y)_9T$ | 57 | 47 | 39 | 36 |
| 5'-(xylo-$X)_9T$ | no $T_m^d$ | no $T_m^d$ | no $T_m^d$ | no $T_m^d$ |

[a]as above for Table 1;
[d]no co-operative melting point $T_m$ was measured in the temperature range 10–95° C.

TABLE 3

| | 5'-d(GZGAZAZGC) vs: | | | | | |
|---|---|---|---|---|---|---|
| | 3'-d(CACTNTACG) | | | | 3'-r(CACUNUACG) | |
| N = Entry | A $T_m$ (° C.) | C $T_m$ (° C.) | T $T_m$ (° C.) | G $T_m$ (° C.) | A $T_m$ (° C.) | C $T_m$ (° C.) |
| 1 Z = T | 28/28* | 11/13* | 12/15* | 19/20* | 28/29* | 10/no $T_m$* |
| 2 Z = Y | 44 | 23 | 27 | 30 | 50 | 33 |
| 3 Z = X | 37 | 19 | 19 | 28 | 45 | 23 |

*results of two identical experiments

The invention claimed is:

1. An oligomer comprising at least one unit comprising an L-ribo-LNA composition of the general formula Ia:

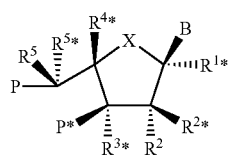

wherein
X is selected from the group consisting of: —O—; —S—; —N($R^{N*}$)—; and —C($R^6R^{6*}$)—;

B is selected from the group consisting of: hydrogen; hydroxy; nucleobases, $C_{1-4}$-alkoxy; $C_{1-4}$-alkyl; $C_{1-4}$-acyloxy; and substituted forms thereof;

P designates a linkage to a succeeding monomer, oligomer, or a 5'-terminal group, said linkage or 5'-terminal group optionally including the substituent $R^5$ or the substituent $R^{5*}$;

P* designates a linkage to a preceding monomer, oligomer, or a 3'-terminal group;

$R^{2*}$ and $R^{4*}$ together represent a biradical consisting of 1–4 groups selected from the group consisting of: —C($R^aR^b$)—; —C($R^a$)=C($R^a$)—; —C($R^a$)=N—; —O—; —Si($R^a$)$_2$—; —S—; —SO$_2$—; —N($R^a$)—; and >C=Z;

wherein Z is selected from —O—, —S—, and —N($R^a$)—; and $R^a$ and $R^b$ each is independently selected from the group consisting of:

hydrogen; hydroxy; nitro; azido; sulphanyl; sulphono; halogen; amino; carbamido; carbamoyl; carboxy; formyl; aryl; $C_{1-2}$-alkyl; $C_{2-12}$-alkenyl; $C_{2-12}$-alkynyl; $C_{1-12}$-alkoxy; $C_{2-12}$-alkenyloxy; $C_{1-12}$-alkoxycarbonyl; $C_{1-12}$-alkylcarbonyl; aryloxy-carbonyl; aryloxy; arylcarbonyl; heteroaryl; heteroaryloxy-carbonyl; heteroaryloxy; heteroarylcarbonyl; mono- di($C_{1-6}$-alkyl)amino; di($C_{1-6}$-alkyl) amino; mono-($C_{1-6}$-alkyl)-amino-carbonyl; di($C_{1-6}$-alkyl)-amino-carbonyl; amino-$C_{1-6}$-alkyl-aminocarbonyl; mono-($C_{1-6}$-alkyl)amino-$C_{1-6}$-alkyl-aminocarbonyl; di($C_{1-6}$-alkyl)amino-$C_{1-6}$-alkyl-aminocarbonyl; $C_{1-6}$-alkyl-carbonylamino; $C_{1-6}$-alkanoyloxy; sulphono; $C_{1-6}$alkylsulphonyloxy; $C_{1-6}$-alkylthio; substituted forms thereof, and a DNA intercalator, a photochemically active group, a thermochemically active group, a chelating group, a reporter group, and a ligand;

or where $R^a$ and $R^b$ together designate methylene olefin (=CH$_2$) or a substituted form thereof; and further wherein:

each of the substituents $R^{1*}$, $R^2$, $R^{3*}$, $R^5$, $R^{5*}$, $R^6$, and $R^{6*}$ is independently selected from the group consisting of:

hydrogen; hydroxy; nitro; azido; sulphanyl; sulphono; halogen; amino; carbamido; carbamoyl; carboxy; formyl; aryl; $C_{1-12}$-alkyl; $C_{2-12}$-alkenyl; $C_{2-12}$-alkynyl; $C_{1-12}$-alkoxy; $C_{2-12}$-alkenyloxy; $C_{1-12}$-alkoxycarbonyl; $C_{1-12}$-alkylcarbonyl; aryloxy-carbonyl; aryloxy; arylcarbonyl; heteroaryl; heteroaryloxy-carbonyl; heteroaryloxy; heteroarylcarbonyl; mono-($C_{1-6}$-alkyl) amino; di($C_{1-6}$-alkyl)amino;

carbamoyl; mono-($C_{1-6}$-alkyl)-amino-carbonyl; di($C_{1-6}$-alkyl)-ammo-carbonyl; amino-$C_{1-6}$-alkyl-aminocarbonyl; mono-($C_{1-6}$-alkyl)amino-$C_{1-6}$-alkyl-aminocarbonyl; di($C_{1-6}$-alkyl)amino-$C_{1-6}$-alkyl-aminocarbonyl; $C_{1-6}$-alkyl-carbonylamino; carbamido; $C_{1-6}$-alkanoyloxy; $C_{1-6}$-alkylsulphonyloxy; $C_{1-6}$-alkylthio; and substituted forms thereof; or wherein two geminal substituents together designate oxo, thioxo, imino or optionally substituted methylene, or together form a spiro biradical consisting of a 1–5 carbon atom alkylene chain which is optionally interrupted and/or terminated by one or more heteroatoms selected from —O—, —S—, and —(NR$^N$)— where R$^N$ is selected from the group consisting of hydrogen; $C_{1-4}$-alkyl; a basic addition salt of $C_{1-4}$-alkyl; an acid addition salt of $C_{1-4}$-alkyl; and substituted forms thereof;

and/or two adjacent non-geminal substituents are bonded together by a double bond, and R$^{N*}$, when present is selected from hydrogen and $C_{1-4}$-alkyl; wherein the L-ribo-LNA composition has an (alpha) configuration.

2. The oligomer according to claim 1, wherein P* is a 3'-terminal group selected from the group consisting of: hydrogen; hydroxy; optionally substituted $C_{1-6}$-alkoxy; optionally substituted $C_{1-6}$-alkylcarbonyloxy; optionally substituted aryloxy; and —W— or —W-A'-, wherein W is selected from —O—, —S—, and —N(R$^H$)—, and wherein R$^H$ is selected from the group consisting of hydrogen and $C_{1-6}$-alkyl; and wherein A' is selected from a DNA intercalator, photochemically active group, thermochemically active group, chelating group, reporter group, and ligand.

3. The oligomer according to any one of claims 1–2, comprising 1 to 50 units.

4. The oligomer according to any one of claims 1–2, wherein B comprises a nucleobase or a functional group protected nucleobase.

5. The oligomer according to any one of claims 1–2, wherein the photochemically active group, the thermochemically active group, the chelating group, the reporter group, or the ligand includes a spacer (K), said spacer comprising a chemically cleavable group.

6. The oligomer according to any of claims 1–2, wherein any P or P* is independently selected from the group consisting of: —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH=, —$CH_2$—$CH_2$—O—, —NR$^H$—$CH_2$—$CH_2$—, —$CH_2$—$CH_2$—NR$^H$—, —$CH_2$—NR$^H$—$CH_2$—, —O—$CH_2$—$CH_2$—NR$^H$—, —NR$^H$—CO—O—, —NR$^H$—CO—NR$^H$—, —NR$^H$—CS—NR$^H$—, —NR$^H$—C(=NR$^H$)—NR$^H$—, —NR$^H$—CO—$CH_2$—NR$^H$—, —O—CO—O—, —O—CO—$CH_2$—O—, —O—$CH_2$—CO—O—, —$CH_2$CO—NR$^H$—, —O—CO—NR$^H$—, —NR$^H$—CO—$CH_2$—, —O—$CH_2$—CO—NR$^H$—, —O—$CH_2$—$CH_2$—NR$^H$—, CH=N—O—, —$CH_2$—NR$^H$—O—, —$CH_2$—O—N=, —$CH_2$—O—NR$_H$—, —CO—NR$^H$—$CH_2$—, —$CH_2$—NR$^H$—O—, —$CH_2$—NR$^H$—CO—, —O—NR$^H$—$CH_2$—, —O—NR$^H$—, —O—$CH_2$—S—, —S—$CH_2$—O—, —$CH_2$—$CH_2$—S—, —O—$CH_2$—$CH_2$—S—, —S—$CH_2$—CH=, —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(—O—)$_2$—O—, —O—S(—O—)$_2$—$CH_2$—, —O—S(O)$_2$—NR$^H$—, —NR$^H$—S(O)$_2$—$CH_2$—, —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R$^H$)—O—, —O—PO(O$CH_3$)—O—, —O—PO(B$H_3$)—O—, —O—PO(NHR$^N$)—O—, —O—P(O)$_2$—NH$^H$—, —NR$^H$—P(O)$_2$—O—, —O—P(ONR$^H$)—O—, and —O—Si(R$^H$)$_2$—O—.

7. A kit comprising a solid support and an oligomer according to any of claims 1–2.

8. A kit comprising an oligomer according to any of claims 1–2 and a label.

9. The kit according to claim 8, wherein the oligomer comprises a fluorophor and a quencher molecule.

10. A kit comprising an affinity pair comprising an oligomer according to any of claims 1–2 and its complementary sequence.

11. An assay, comprising:
    a. contacting one or more naturally occurring or synthetic double-stranded or single-stranded nucleic acids, with an oligomer according to any one of claims 1–2 and
    b. detecting binding of the oligomer to the oligonucleotide.

12. The assay according to claim 11, wherein the oligomer comprises a fluorophor and a quencher, the fluorophor providing a fluorescent signal and the quencher being positioned such that the hybridized state of the oligonucleotide can be distinguished from the unbound state of the oligonucleotide by a change in the fluorescent signal.

13. A method for making an oligomer comprising:
    providing an L-Ribo LNA composition according to any of claims 1–2 and incorporating the same into an oligomer using a phosphoramidite method, a phosphortriester method, an H-phosphonate method or an enzymatic synthesis method.

14. The method according to claim 13, wherein the L-Ribo-LNA nucleoside is included at the 3'-end or 5-end of the oligomer.

15. The method according to claim 13, wherein the oligomer comprises one or more units according to any of claims 1–2.

16. The method according to claim 14, wherein the method is performed in solution or on a solid phase.

17. The method according to claim 13, wherein the oligomers are linear, branched or circular.

18. The oligomer of claim 1, wherein the biradical is independently selected from
—$(CH_2)_{0-1}$—O—$(CH_2)_{1-3}$—, —$(CH_2)_{0-1}$—S—$(CH_2)_{1-3}$—, and —$(CH_2)_{0-1}$—N(R$^N$)—$(CH_2)_{1-3}$—.

19. The oligomer of claim 18, wherein the biradical is independently selected from —O—$CH_2$, —S—$CH_2$, and —N(R$^N$)—$CH_2$—.

20. A method of using the oligomer of claim 1 or 2 as a nucleic acid binding agent, the method comprising the steps of contacting the oligomer with the nucleic acid and forming a complex to bind the nucleic acid.

21. The method of claim 20, wherein the nucleic acid is RNA.

22. The method of claim 21, wherein the RNA is selected from tRNA, rRNA, snRNA, and scRNA.

23. The oligomer of claim 1, wherein the succeeding monomer is a naturally occuring nucleoside, peptide nucleic acid (PNA), or a locked nucleic acid (LNA).

24. The oligomer of claim 1, wherein the succeeding oligomer comprises a naturally occuring nucleoside, peptide nucleic acid (PNA), or a locked nucleic acid (LNA).

25. The oligomer of claim 1, wherein the proceeding monomer is a naturally occuring nucleoside, peptide nucleic acid (PNA), or a locked nucleic acid (LNA).

26. The oligomer of claim 1, wherein the proceeding oligomer comprises a naturally occuring nucleoside, peptide nucleic acid (PNA), or a locked nucleic acid (LNA).

27. A composition having the following formula IIa:

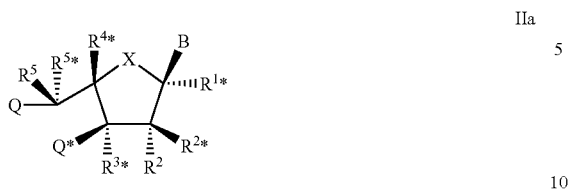

wherein B comprises a nucleobase, DNA intercalator, a photochemically active group, a thermochemically active group, a chelating group, a reporter group, or a ligand;

X is selected from —O—, —S—, —N($R^N$)—, and —C($R^6R^{6*}$)—; each of Q and Q* is independently selected from the group consisting of: hydrogen; azido; halogen; cyano; nitro; hydroxy; carboxy; carboxymethyl; sulphono; sulphonomethyl; hydroxymethyl; monophosphate; diphosphate; triphosphate; mercapto; amino; aminomethyl; Prot-O—; Prot-O—CH$_2$—; Act-O—; Act-O—CH$_2$—; Prot-S—; Act-S—; Prot-N($R^H$)—; Act-N($R^H$)—; Prot-N($R^H$)—CH$_2$—; Act-N($R^H$)—CH$_2$—; mono-($C_{1-6}$-alkyl)amino; di($C_{1-6}$-alkyl)amino; $C_{1-6}$-alkylthio; $C_{1-6}$-alkoxy, $C_{1-6}$-alkyl, $C_{2-6}$-alkenyl, $C_{2-6}$-alkenyloxy, $C_{2-6}$-alkynyl, $C_{2-6}$-alkynyloxy, and substituted forms thereof; wherein Prot is a protection group for —OH, —SH, and —NH($R^H$), respectively, Act is an activation group for —OH, —SH, and —NH($R^H$), respectively, and $R^H$ is selected from hydrogen and $C_{1-6}$-alkyl; and $R^{2*}$ and $R^{4*}$ together designate a biradical selected from —O—, —(CR*R*)$_{r+s}$—, —(CR*R*)$_r$—O—(CR*R*)$_s$—, —(CR*R*)$_r$—S—(CR*R*)$_s$—, —(CR*R*)$_r$—N(R*)—(CR*R*)$_s$—, —O—(CR*R*)$_{r+s}$—O—, —S—(CR*R*)$_{r+s}$—O—, —O—(CR*R*)$_{r+s}$—S—, —N(R*)—(CR*R*)$_{r+s}$—O—, —O—(CR*R*)$_{r+s}$—N(R*)—, —S—(CR*R*)$_{r+s}$—S—, —N(R*)—(CR—R*)$_{r+s}$—N(R*), —N(R)—(CR*R*)$_{r+s}$—S—, and —S—(CR*R*)$_{r+s}$—N(R*)—; wherein each R* is independently selected from hydrogen, halogen, azido, cyano, nitro, hydroxy, mercapto, amino, mono-($C_{1-6}$-alkyl)amino; di($C_{1-6}$-alkyl)amino; $C_{1-6}$-alkoxy, $C_{1-6}$-alkyl, and substituted forms thereof;

and/or two adjacent (non-geminal) R* may together designate a double bond, and each of r and s is 0–3 with the proviso that the sum r+s is 1–4;

each of substituents $R^{1*}$, $R^2$, $R^{3*}$, $R^4$, $R^{5*}$, $R^6$, and $R^{6*}$ is independently selected from the group consisting of: hydrogen; hydroxy; halogen; nitro; azido; sulphanyl; sulphono; carboxy; carbamoyl; carbamido; amino; formyl; aryl; aryloxy; arylcarbonyl; heteroaryl; heteroaryloxy-carbonyl; heteroaryl-oxy; heteroarylcarbonyl; $C_{1-12}$-alkyl; $C_{2-12}$-alkenyl; $C_{2-12}$-alkynyl; $C_{1-12}$-alkoxy; $C_{2-12}$-alkenyloxy; $C_{1-12}$-alkoxycarbonyl; $C_{1-12}$-alkylcarbonyl; aryl-oxy-carbonyl, mono-($C_{1-6}$-alkyl)amino; di-($C_{1-6}$-alkyl)amino; mono-($C_{1-6}$-alkyl)-amino-carbonyl; di-($C_{1-6}$-alkyl)-amino-carbonyl; 1-6-alkyl-aminocarbonyl; mono-($C_{1-6}$-alkyl)amino-$C_{1-6}$-alkyl-aminocarbonyl; di-($C_{1-6}$-alkyl)amino-$C_{1-6}$-alkyl-aminocarbonyl; $C_{1-6}$-alkyl-carbonylamino; $C_{1-6}$-alkanoyloxy; $C_{1-6}$-alkylsulphonyloxy; $C_{1-6}$-alkylthio; and substituted forms thereof; or wherein two geminal substituents together designate oxo, thioxo, imino, or optionally substituted methylene, or together form a spiro biradical consisting of a 1–5 carbon alkylene chain which is optionally interrupted and/or terminated by one or more heteroatoms selected from —O—, —S—, and —(NR$^N$)— wherein R$^N$ is selected from the group consisting of hydrogen; $C_{1-4}$-alkyl; a basic addition salt of $C_{1-4}$-alkyl; an acid addition salt of $C_{1-4}$-alkyl; and substituted forms thereof; and/or two adjacent non-geminal substituents are bonded together by a double bond; and further, wherein any chemical group which is reactive under the conditions prevailing in oligonucleotide synthesis, is optionally functional group protected, and $R^{N*}$, when present is selected from hydrogen and $C_{1-4}$-alkyl; wherein the composition has an α(alpha) configuration.

28. The composition of claim 27, wherein the biradical is independently selected from —(CH$_2$)$_{0-1}$—O—(CH$_2$)$_{1-3}$—, —(CH$_2$)$_{0-1}$—S—(CH$_2$)$_{1-3}$—, and —(CH$_2$)$_{0-1}$—N($R^N$)—(CH$_2$)$_{1-3}$—.

29. The composition of claim 28, wherein the biradical is independently selected from O—CH$_2$, S—CH$_2$, and —N($R^N$)—CH$_2$—.

* * * * *